US011943999B2

(12) United States Patent
Lin et al.

(10) Patent No.: US 11,943,999 B2
(45) Date of Patent: *Mar. 26, 2024

(54) ORGANIC ELECTROLUMINESCENT MATERIALS AND DEVICES

(71) Applicant: UNIVERSAL DISPLAY CORPORATION, Ewing, NJ (US)

(72) Inventors: Chun Lin, Yardley, PA (US); Chuanjun Xia, Lawrenceville, NJ (US); Jui-Yi Tsai, Newtown, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 548 days.

This patent is subject to a terminal disclaimer.

(21) Appl. No.: 17/208,662

(22) Filed: Mar. 22, 2021

(65) Prior Publication Data

US 2021/0210701 A1 Jul. 8, 2021

Related U.S. Application Data

(60) Continuation of application No. 16/927,297, filed on Jul. 13, 2020, now Pat. No. 10,985,331, which is a
(Continued)

(51) Int. Cl.
*H10K 85/30* (2023.01)
*C07D 209/82* (2006.01)
(Continued)

(52) U.S. Cl.
CPC ......... *H10K 85/346* (2023.02); *C07D 209/82* (2013.01); *C07D 213/69* (2013.01); *C07D 233/54* (2013.01); *C07D 235/04* (2013.01); *C07D 401/12* (2013.01); *C07F 7/0814* (2013.01); *C07F 15/0086* (2013.01); *C07F 15/0093* (2013.01); *C09K 11/06* (2013.01);
(Continued)

(58) Field of Classification Search
CPC .................................................. H10K 85/346
See application file for complete search history.

(56) References Cited

U.S. PATENT DOCUMENTS 4,769,292 A  9/1988 Tang et al.
5,061,569 A  10/1991 VanSlyke et al.
(Continued)

FOREIGN PATENT DOCUMENTS

EP  0650955  5/1995
EP  1725079  11/2006
(Continued)

OTHER PUBLICATIONS

Lai, Shiu-Lun, et al., "High Efficiency White Organic Light-Emitting Devices Incorporating Yellow Phosphorescent Platinum(II) Complex and Composite Blue Host," Advanced Functional Materials, vol. 23, Issue 21, Nov. 6, pp. 2013, 23, 5168-5178.
(Continued)

*Primary Examiner* — Sean M DeGuire
(74) *Attorney, Agent, or Firm* — DUANE MORRIS LLP; Gregory M. Lefkowitz

(57) ABSTRACT

Novel Pt tetradentate complexes having Pt—O bond is disclosed. These complexes are useful as emitters in phosphorescent OLEDs.

20 Claims, 4 Drawing Sheets

FORMULA I

Related U.S. Application Data continuation of application No. 16/154,864, filed on Oct. 9, 2018, now Pat. No. 10,749,122, which is a division of application No. 14/565,576, filed on Dec. 10, 2014, now Pat. No. 10,135,008.

(60) Provisional application No. 61/924,340, filed on Jan. 7, 2014.

(51) Int. Cl.
| | |
|---|---|
| C07D 213/69 | (2006.01) |
| C07D 233/54 | (2006.01) |
| C07D 235/04 | (2006.01) |
| C07D 401/12 | (2006.01) |
| C07F 7/08 | (2006.01) |
| C07F 15/00 | (2006.01) |
| C09K 11/06 | (2006.01) |
| H10K 50/11 | (2023.01) |
| H10K 101/10 | (2023.01) |

(52) U.S. Cl.
CPC ...... *H10K 50/11* (2023.02); *C09K 2211/1007* (2013.01); *C09K 2211/1029* (2013.01); *C09K 2211/1044* (2013.01); *C09K 2211/185* (2013.01); *H10K 2101/10* (2023.02)

(56) References Cited

U.S. PATENT DOCUMENTS

| | | | |
|---|---|---|---|
| 5,247,190 | A | 9/1993 | Friend et al. |
| 5,703,436 | A | 12/1997 | Forrest et al. |
| 5,707,746 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,442,797 | B2 | 10/2008 | Itoh et al. |
| 7,445,855 | B2 | 11/2008 | Mackenzie et al. |
| 7,534,505 | B2 | 5/2009 | Lin et al. |
| 10,135,008 | B2 | 11/2018 | Lin |
| 10,749,122 | B2 | 8/2020 | Lin |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0152802 | A1 | 8/2003 | Tsuboyama et al. |
| 2003/0162053 | A1 | 8/2003 | Marks et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0227112 | A1 | 10/2005 | Ise et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0073359 | A1 | 4/2006 | Ise et al. |
| 2006/0182992 | A1 | 8/2006 | Nii et al. |
| 2006/0202194 | A1 | 9/2006 | Jeong et al. |
| 2006/0240279 | A1 | 10/2006 | Adamovich et al. |
| 2006/0261923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220266 | A1 | 9/2008 | Xia et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0046731 | A1 | 2/2009 | Nishimura et al. |
| 2009/0101870 | A1 | 4/2009 | Prakash et al. |
| 2009/0108737 | A1 | 4/2009 | Kwong et al. |
| 2009/0116316 | A1 | 5/2009 | Zheng et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2012/0215001 | A1* | 8/2012 | Li .................. C09K 11/06 546/4 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 8/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 6/2008 |
| WO | 2008101842 | 8/2008 |
| WO | 2008132085 | 11/2008 |
| WO | 2005123873 | 12/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |

(56) References Cited

FOREIGN PATENT DOCUMENTS

| WO | 2009062578 | 5/2009 |
|---|---|---|
| WO | 2009066778 | 5/2009 |
| WO | 2009066779 | 5/2009 |
| WO | 2009063833 | 6/2009 |
| WO | 2009086028 | 7/2009 |
| WO | 2009100991 | 8/2009 |
| WO | 2009/111299 | 9/2009 |

OTHER PUBLICATIONS

Kui, Steven C.F., et al., "Robust Phosphorescent Platinum(II) Complexes Containing Tetradentate O^ N^ C^ N Ligands: Excimeric Excited State and Application in Organic White-Light-Emitting Diodes," Chemistry—a European Journal, vol. 19, Issue 1, pp. 69-73, Jan. 2, 2013.

Meyer, Anke, et al., "Platinum(II) Complexes with Tetradentate Dianionic (O^ C*^ C*^ O)-Ligands," Organometallics, 2011, 30 (11), pp. 2880-2985.

Boydston, Andrew J. et al., "Synthesis and Study of Bidentate Benzimidazolylidene—Group 10 Metal Complexes and Related Main-Chain Organometallic Polymers" Organometallics, 2006, 25, 6087-6098.

Extended European Search Report dated Jun. 13, 2017 for corresponding EP Patent Application No. 17161875.4.

J. Atzrodt et al., "The Renaissance of H/D Exchange" Angew. Chem. Int. Ed. 2007, 46. pp. 7744-7765.

Rosenani S.M. Anwarul Haque "Silver, mercury and ruthenium complexes of N-heterocyclic carbene linked cyclophanes" Thesis presented for the degree of Doctor of Philosophy dated Feb. 2007.

Office Action dated Oct. 21, 2020 in orresponding Korean Patent Application No. 10-2014-0190482.

Adachi, Chihaya et al., "Organic Electrolumines Device Having a Hole Conductor as an Emitting Layer," Appl. Phys Lett., 56(15): 1488-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183603-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao Zhiqiang et al., "Bright-Blue Electroluminescence From a Silyl-Substitued ter-(phenylene-vinylene) derivative," Appl. Phys. Lett., 74(6): 885-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(hydroxybenzo[h]quinolinato) beryllium as an Emitter," Chem. Lett., 906-906 (1993).

Holmes, R.J. et al., "Blue Organic Electrophosphorascence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett. 780(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuniko, "1,3,6-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4'4''-Tri(N-carbazolyl)triphenylamine (TCTA) and 4,4',4''-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-on voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota, Yasuhiko, "5,5'-Bis(dimesitylboryl0-2,2'-bithiophene and 5,5''-Bis (dimesitylboryl)-2,2'5',2''-terthiophene as a Novel Family of Electron-Transporting Amorphous Molecular Materiais," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063 04-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S, et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron Transport Property of Perfluorinated Phenylene Dendrimers," J. Am. Chem. Soc., 122(8):1832-1833 (2000).

(56) References Cited

OTHER PUBLICATIONS

Salbeck, J. et al., "Low Molecular Organic Glasses for Blue Electroluminescence," Synthetic Metals, 91: 209-215 (1997).

Shirota, Yasuhiko et al., "Starburst Molecules Based on pi-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).

Sun, Yiru and Forrest, Stephen R., "High Efficiency White Organic Light Emitting Devices with Three Separate Phosphorescent Emission Layers," Appl. Phys. Lett, 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 88:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69(15):2160-2162 (1998).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Cotour, Chem. Commun., 2908-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

FORMULA I

ORGANIC ELECTROLUMINESCENT MATERIALS AND DEVICES

CROSS-REFERENCE TO RELATED APPLICATIONS

This application is a continuation of U.S. patent application Ser. No. 16/927,297, filed Jul. 13, 2020, which is a continuation of U.S. patent application Ser. No. 16/154,864, filed Oct. 9, 2018, now U.S. Pat. No. 10,749,122, which is a divisional of U.S. patent application Ser. No. 14/565,576, filed on Dec. 10, 2014, now U.S. Pat. No. 10,135,008, which claims priority under 35 U.S.C. § 119(e) to U.S. Provisional Application Ser. No. 61/924,340, filed Jan. 7, 2014, the disclosures of which are herein expressly incorporated by reference in their entirety.

PARTIES TO A JOINT RESEARCH AGREEMENT

The claimed invention was made by, on behalf of, and/or in connection with one or more of the following parties to a joint university corporation research agreement: The Regents of the University of Michigan, Princeton University, University of Southern California, and Universal Display Corporation. The agreement was in effect on and before the date the claimed invention was made, and the claimed invention was made as a result of activities undertaken within the scope of the agreement.

FIELD OF THE INVENTION

The present invention relates to compounds for use as phosphorescent emitters and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

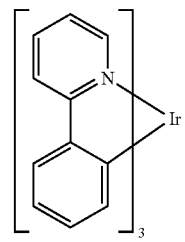

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a compound having a Pt tetradentate structure, having the formula:

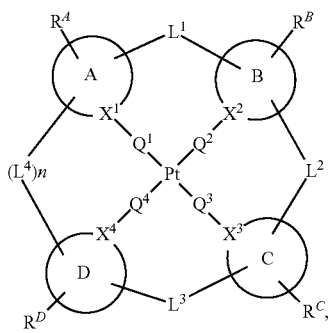

Formula I, is disclosed, wherein rings A, B, C, and D each independently represent a 5-membered or 6-membered carbocyclic or heterocyclic ring;

wherein $R^A$, $R^B$, $R^C$, and $R^D$ each independently represent mono, di, tri, or tetra-substitution, or no substitution;

wherein $L^1$, $L^2$, and $L^3$ are each independently selected from the group consisting of a direct bond, BR, NR, PR, O, S, Se, C=O, S=O, $SO_2$, CRR', SiRR', GeRR', and combinations thereof, wherein when n is 1, $L^4$ is selected from the group consisting of a direct bond, BR, NR, PR, O, S, Se, C=O, S=O, $SO_2$, CRR', SiRR', GeRR', and combinations thereof, when n is 0, $L^4$ is not present;

wherein $R^A$, $R^B$, $R^C$, $R^D$, R, and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein any adjacent $R^A$, $R^B$, $R^C$, $R^D$, R, and R' are optionally joined to form a ring;

wherein $X^1$, $X^2$, $X^3$, and $X^4$ each independently selected from the group consisting of carbon and nitrogen;

wherein one of $Q^1$, $Q^2$, $Q^3$, and $Q^4$ is oxygen, the remaining three of $Q^1$, $Q^2$, $Q^3$, and $Q^4$ each represents a direct bond so that Pt directly bonds to three of $X^1$, $X^2$, $X^3$, and $X^4$; and wherein when $L^1$, $L^2$, $L^3$, or $L^4$ represents a direct bond, the direct bond is not a C—C bond.

According to another embodiment, a device comprising one or more organic light emitting devices is also provided. At least one of the one or more organic light emitting devices comprises an anode, a cathode, and an organic layer, disposed between the anode and the cathode, wherein the organic layer includes a compound having Formula I as defined herein including all of its variations.

According to yet another embodiment, a formulation comprising a compound having Formula I as defined herein including all of its variations, is provided.

According to another embodiment, a novel method for forming a metal-carbene bond is disclosed.

The novel Pt tetradentate complexes having Pt—O bond disclosed herein are useful as emitters in phosphorescent OLEDs.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
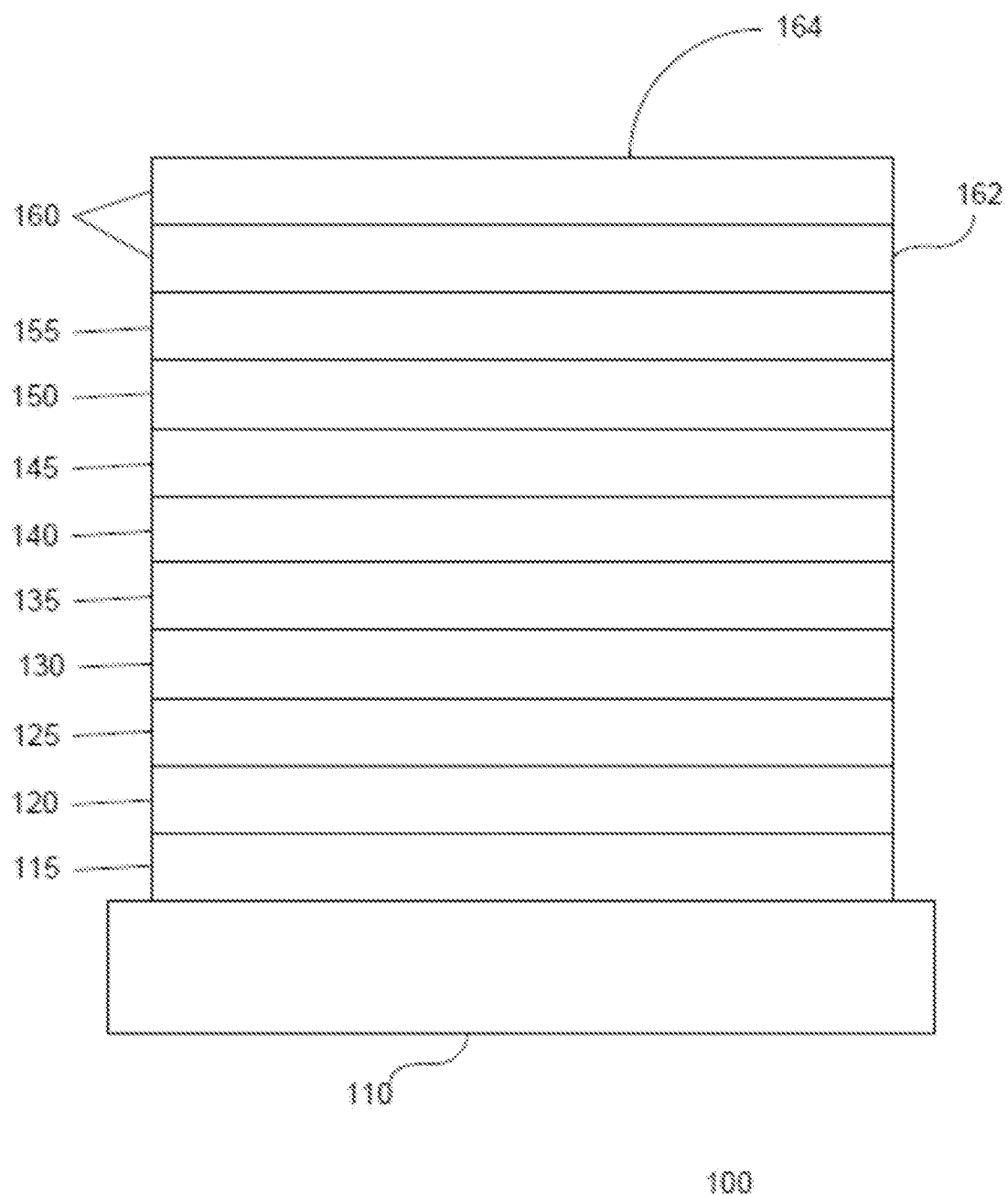
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
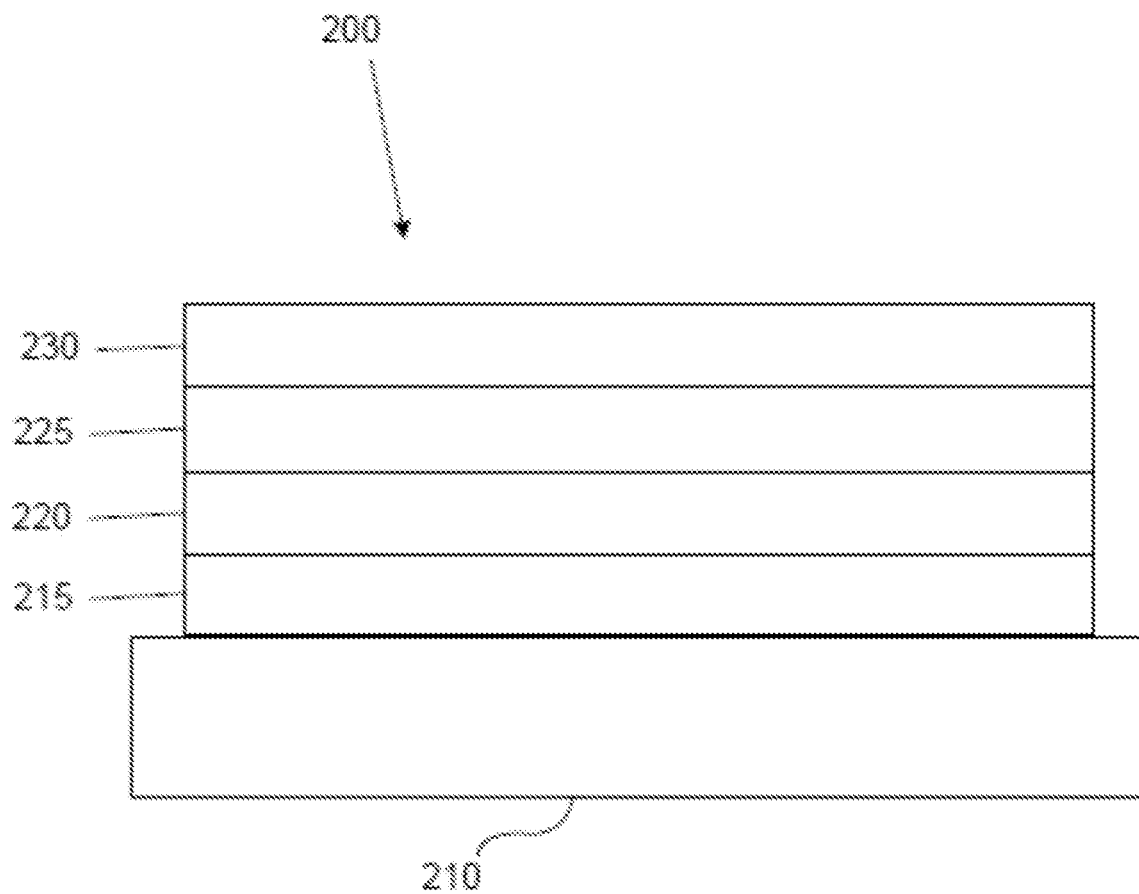
FIG. 2 shows an inverted organic light emitting device that does not have a separate electron transport layer.
Figure 3:
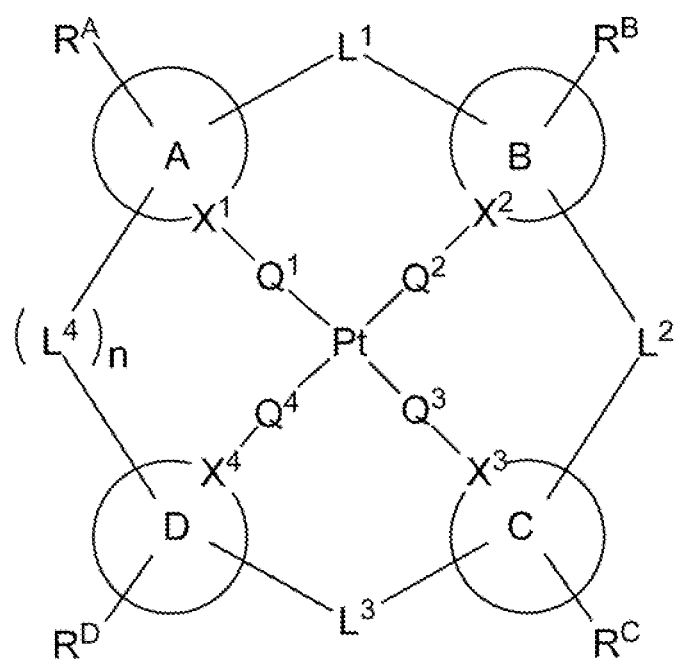
FIG. 3 shows Formula I as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, microdisplays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[fh]quinoxaline and dibenzo[fh]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

Tetradentate platinum complexes can be used as emitters in phosphorescent OLEDs. These complexes have a single ligand that has four coordination sites, enabling versatile materials design. The known tetradentate platinum complexes such as tetradentate platinum complex coordinating to a ligand with two neutral nitrogen donors, one anionic carbon donor and one anionic oxygen donor (Advanced Functional Materials, 2013, 23, 5168 and Chemistry a European Journal, 2013, 19, 69) have shown high PLQY and high EQE in OLED devices. However, because of the conjugation and low triplet energy of the ligands, only green and longer wavelength emission can be achieved. In the present disclosure, the inventors have formulated tetradentate platinum complexes with high triplet energy ligands. These novel complexes comprise a Pt—O bond.

According to an aspect of the present disclosure, a compound having a Pt tetradentate structure having the formula:

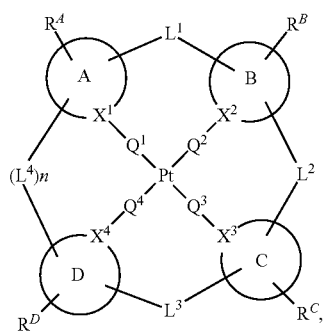

Formula I, is disclosed. In Formula I, rings A, B, C, and D each independently represent a 5-membered or 6-membered carbocyclic or heterocyclic ring; wherein $R^A$, $R^B$, $R^C$, and $R^D$ each independently represent mono, di, tri, or tetra-substitution, or no substitution; wherein $L^1$, $L^2$, and $L^3$ are each independently selected from the group consisting of a direct bond, BR, NR, PR, O, S, Se, C=O, S=O, SO$_2$, CRR', SiRR', GeRR', and combinations thereof, wherein when n is 1, $L^4$ is selected from the group consisting of a direct bond, BR, NR, PR, O, S, Se, C=O, S=O, SO$_2$, CRR', SiRR', GeRR', and combinations thereof, when n is 0, $L^4$ is not present; wherein $R^A$, $R^B$, $R^C$, $R^D$, R, and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein any adjacent $R^A$, $R^B$, $R^C$, $R^D$, R, and R' are optionally joined to form a ring; wherein $X^1$, $X^2$, $X^3$, and $X^4$ each independently selected from the group consisting of carbon and nitrogen;

wherein one of $Q^1$, $Q^2$, $Q^3$, and $Q^4$ is oxygen, the remaining three of $Q^1$, $Q^2$, $Q^3$, and $Q^4$ each represents a direct bond so that Pt directly bonds to three of $X^1$, $X^2$, $X^3$, and $X^4$; and wherein when $L^1$, $L^2$, $L^3$, or $L^4$ represents a direct bond, the direct bond is not a C—C bond.

In one embodiment of the compound, wherein two of $X^1$, $X^2$, $X^3$, and $X^4$ that directly bond to Pt are carbon thus forming Pt—C bonds, and one of $X^1$, $X^2$, $X^3$, and $X^4$ that directly bond to Pt is nitrogen. In another embodiment, wherein the two Pt—C bonds are in cis configuration.

In one embodiment of the compound, $L^1$, $L^2$, and $L^3$ are each independently selected from the group consisting of a direct bond, NR, O, CRR', SiRR', and combinations thereof, and wherein when n is 1, $L^4$ is selected from the group consisting of a direct bond, NR, O, CRR', SiRR', and combinations thereof.

In another embodiment of the compound, R and R' are each independently selected from the group consisting of hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, and combinations thereof.

In one embodiment, the compound has a neutral charge.

In one embodiment, the compound has at least one Pt-carbene bond.

In one embodiment of the compound, n is 0. In another embodiment of the compound, n is 1.

In one embodiment of the compound, one of the rings A, B, C, and D is phenyl when said ring is bonded to one of the $Q^1$, $Q^2$, $Q^3$, and $Q^4$ that is oxygen.

In one embodiment of the compound, the rings A, B, C, and D are each independently selected from the group consisting of phenyl, pyridine, and imidazole.

In one embodiment of the compound, when $L^1$, $L^2$, $L^3$, or $L^4$ represents a direct bond, the direct bond is a C—N bond.

In one embodiment of the compound, at least one of $L^1$, $L^2$, $L^3$, and $L^4$ is not a direct bond.

In another embodiment of the compound, the compound is selected from the group consisting of:

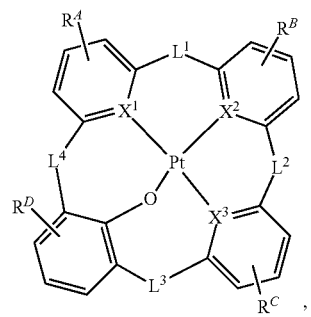

-continued
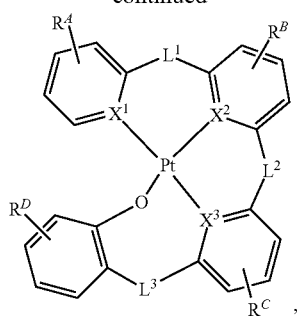,
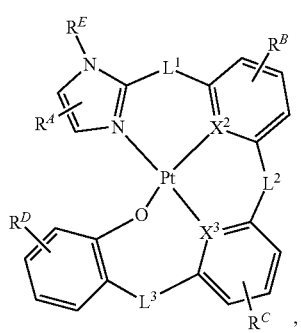,
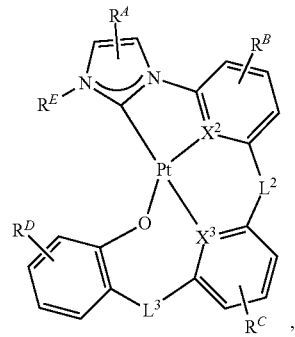,
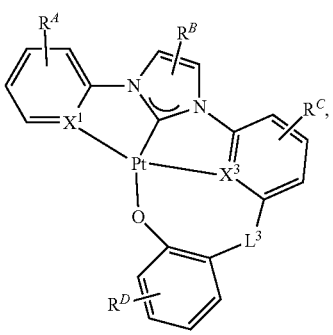,
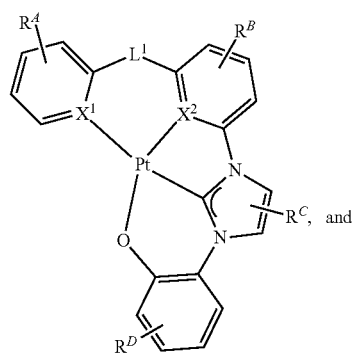 and
-continued
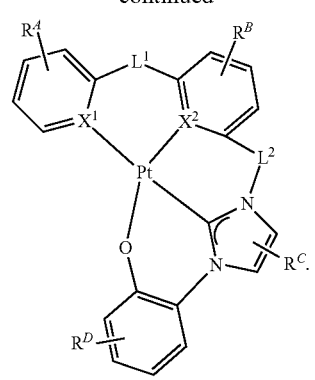.
In another embodiment of the compound, the compound is selected from the group consisting of:
Compound 1
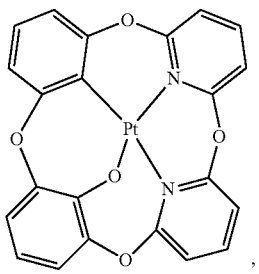,
Compound 2
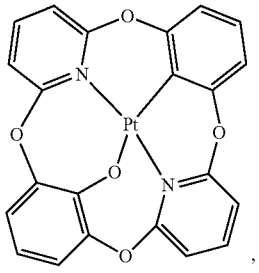,
Compound 3
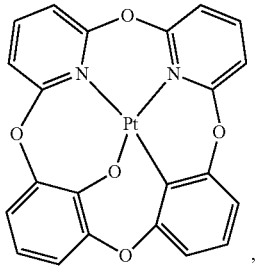,
Compound 4
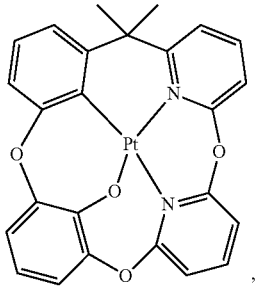, Compound 5
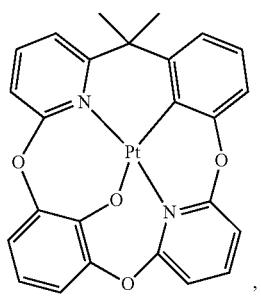
Compound 6
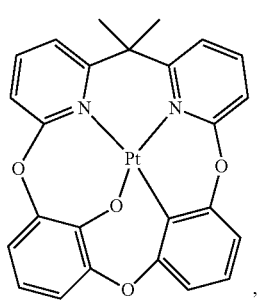
Compound 7
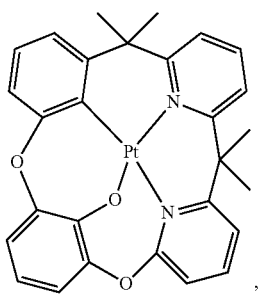
Compound 8
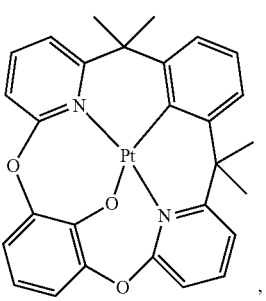
Compound 9
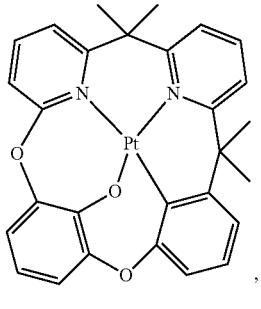
Compound 10
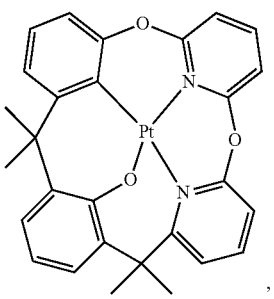
Compound 11
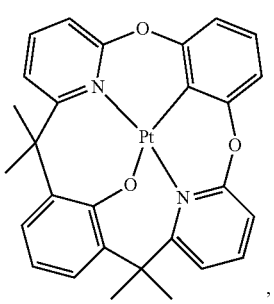
Compound 12
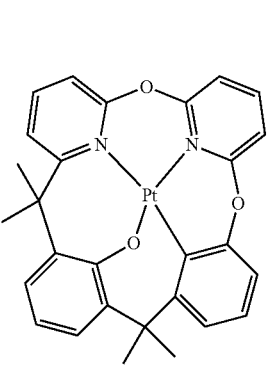
Compound 14
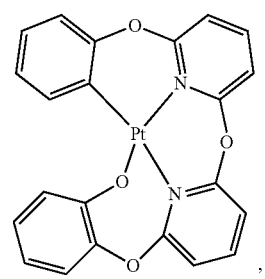
Compound 15
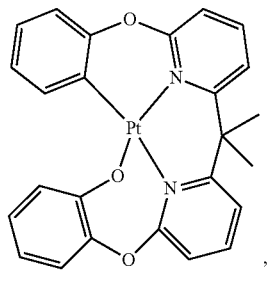

Compound 16
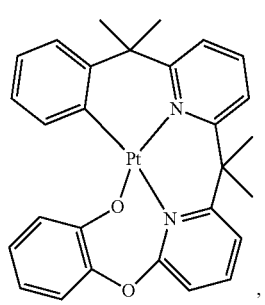
Compound 17
Compound 18
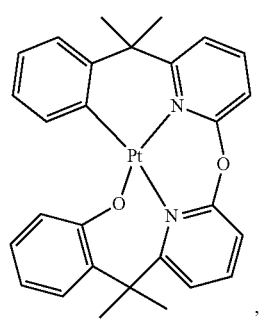
Compound 19
Compound 20
Compound 21
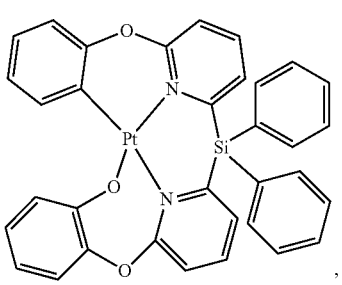
Compound 22
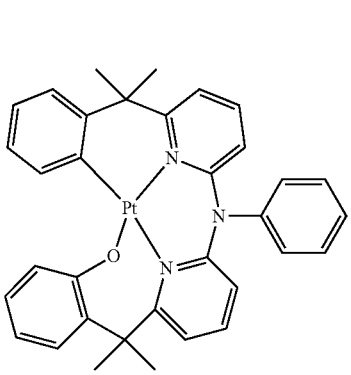
Compound 23
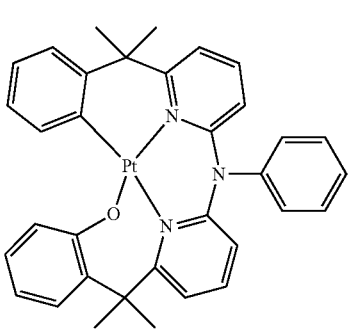
Compound 24
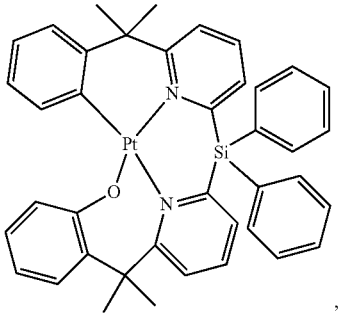
Compound 25
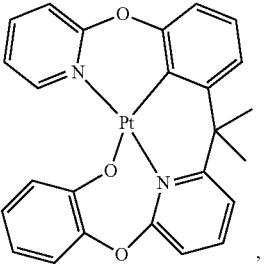

-continued
Compound 26
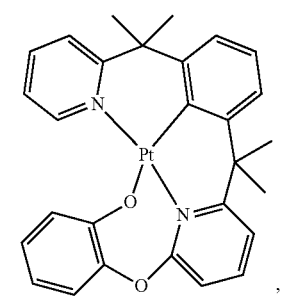
Compound 27
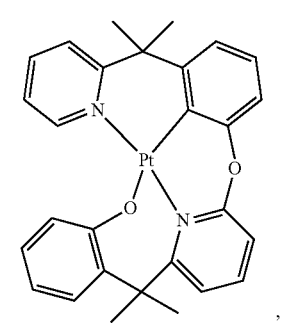
Compound 28
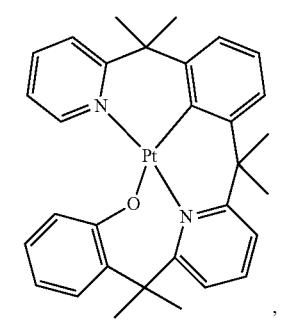
Compound 29
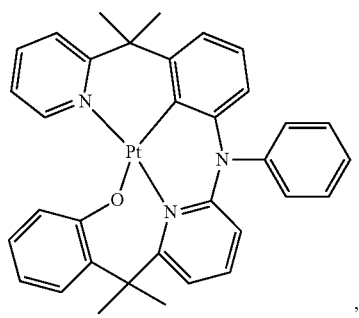
Compound 30
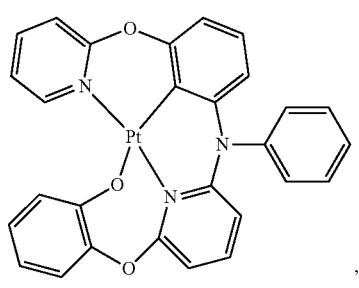
-continued
Compound 31
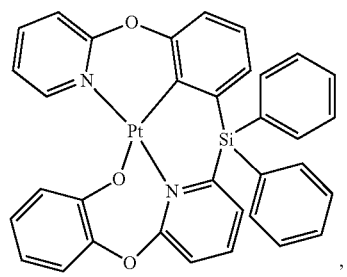
Compound 32
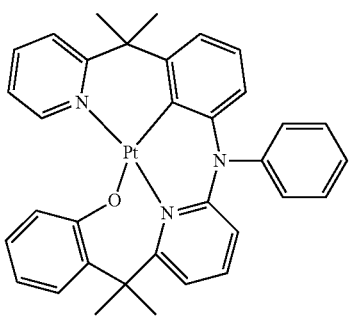
Compound 33
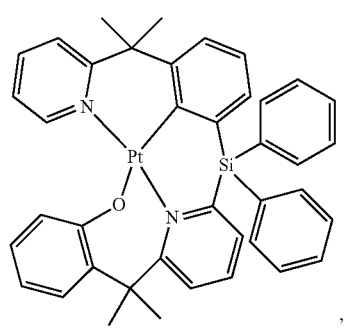
Compound 34
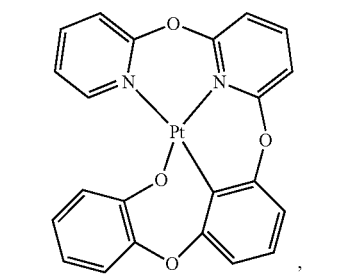
Compound 35
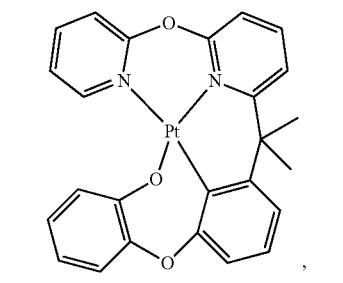

Compound 36
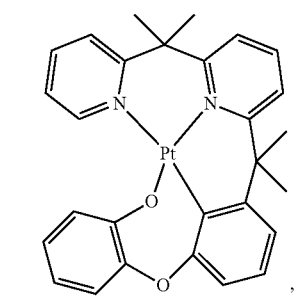
Compound 37
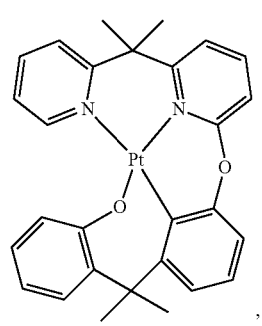
Compound 38
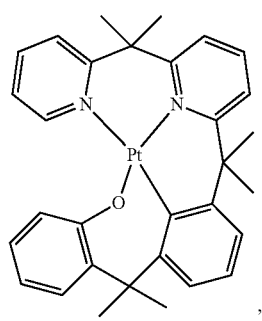
Compound 39
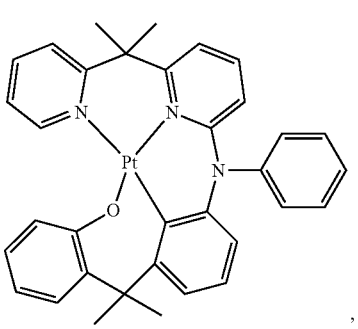
Compound 40
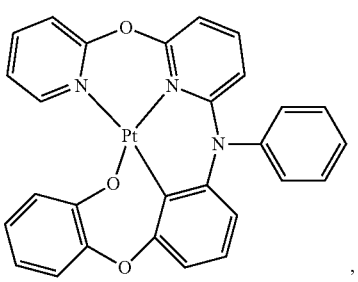
Compound 41
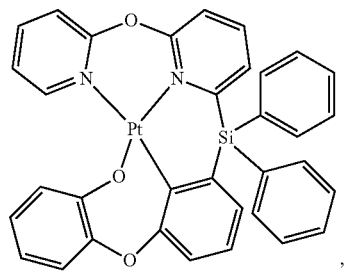
Compound 42
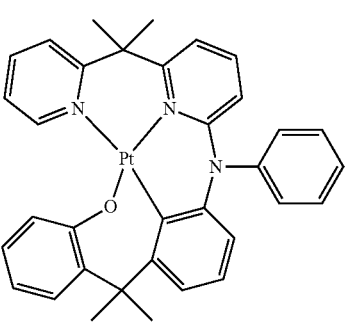
Compound 43
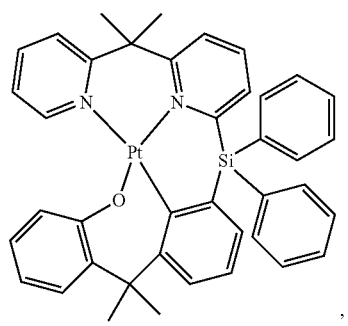
Compound 44
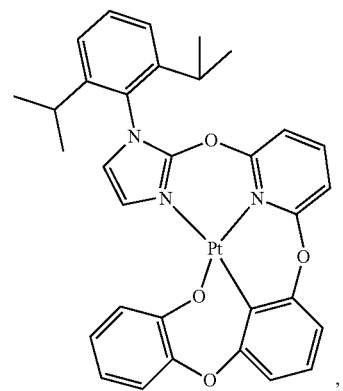

Compound 45
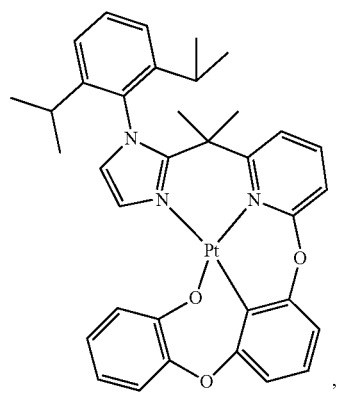
Compound 46
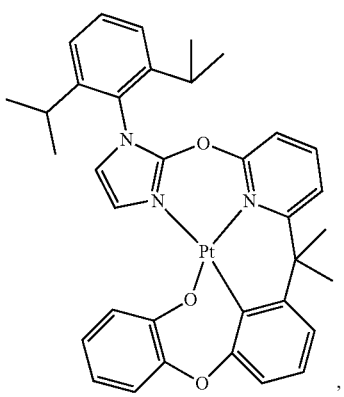
Compound 47
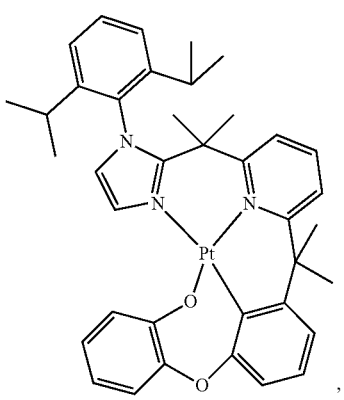
Compound 48
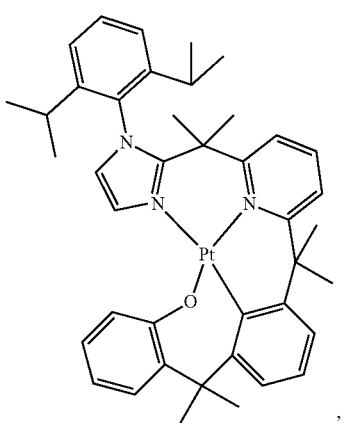
Compound 49
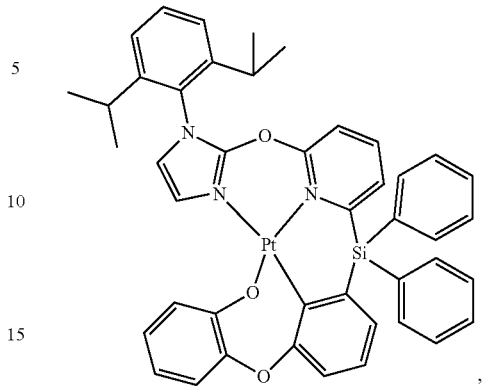
Compound 50
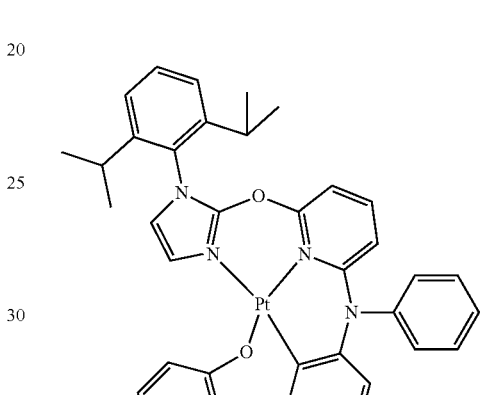
Compound 51
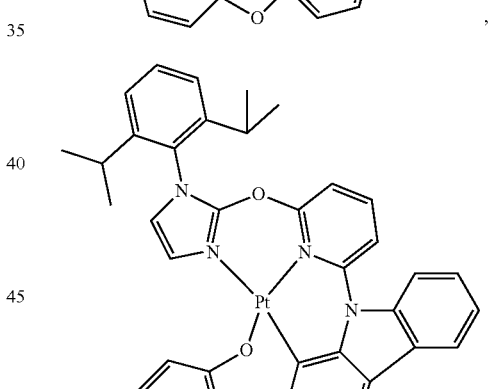
Compound 52
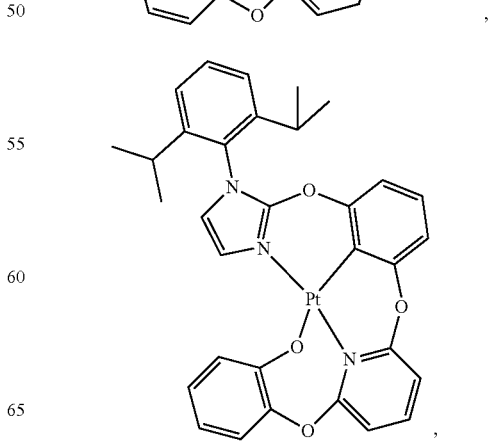

-continued
Compound 53
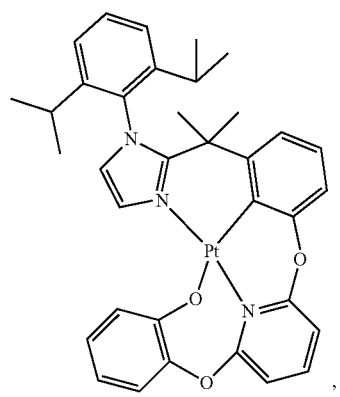
Compound 54
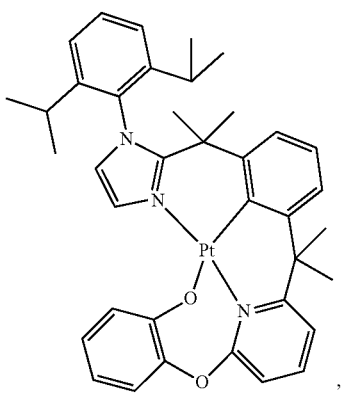
Compound 55
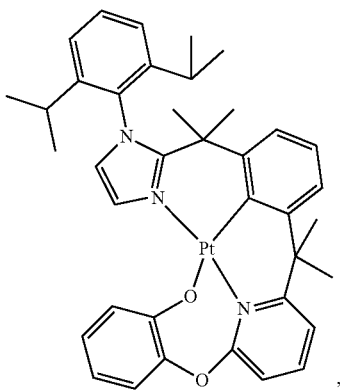
Compound 56
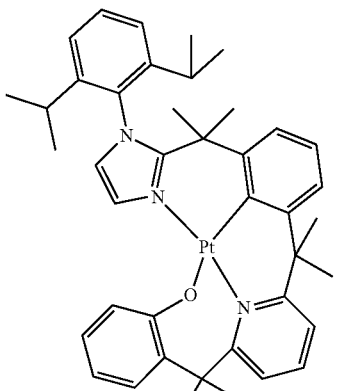
-continued
Compound 57
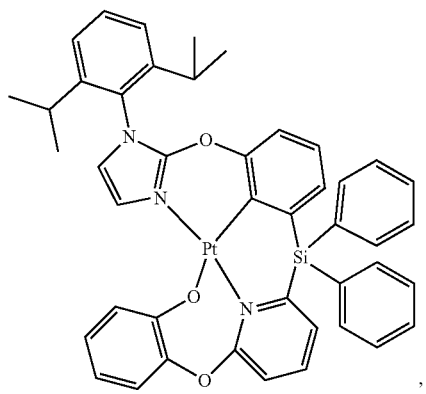
Compound 58
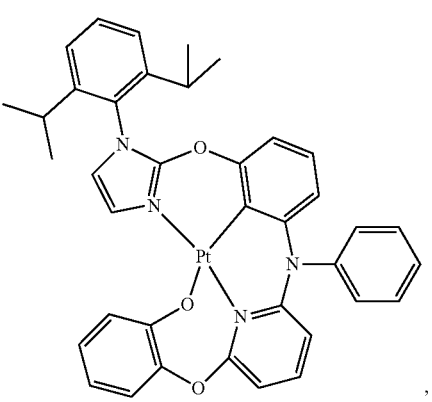
Compound 59
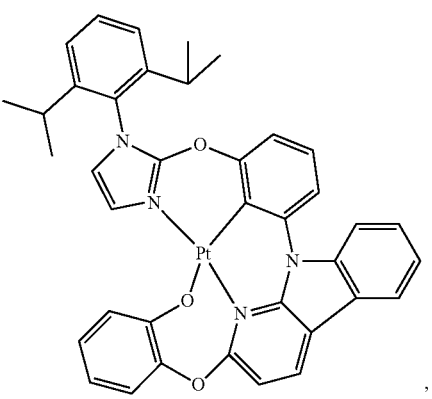
Compound 60
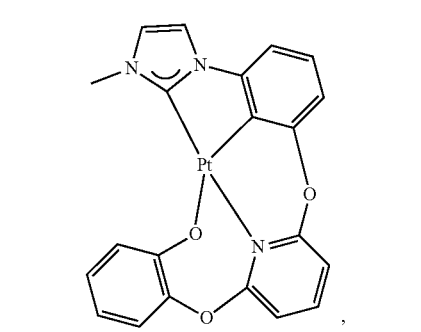

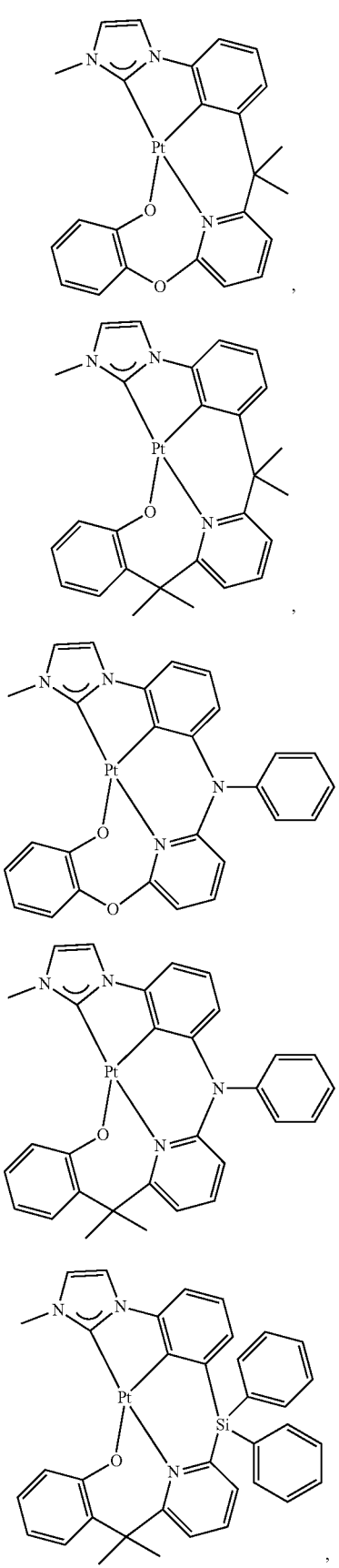
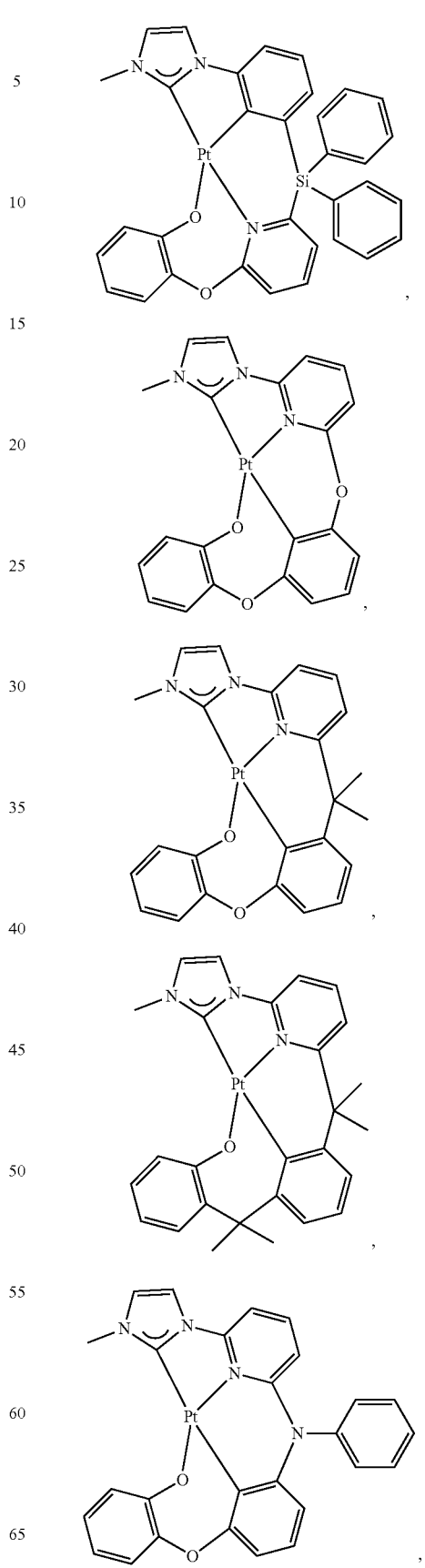

Compound 71
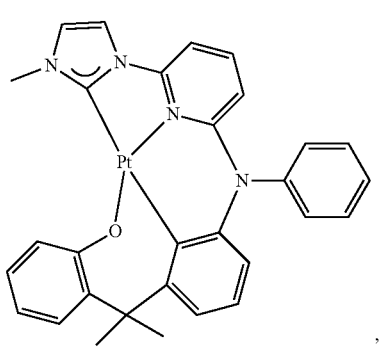
Compound 72
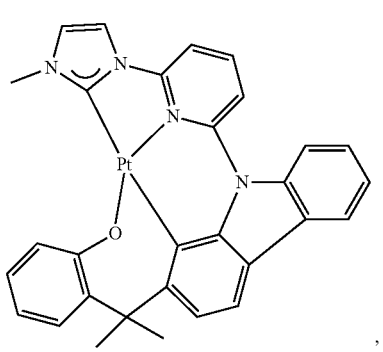
Compound 73
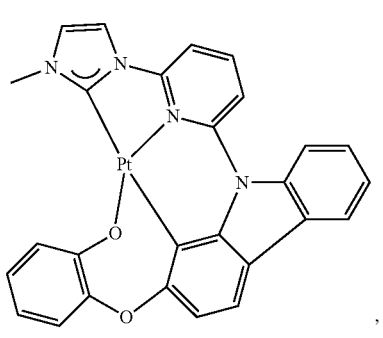
Compound 74
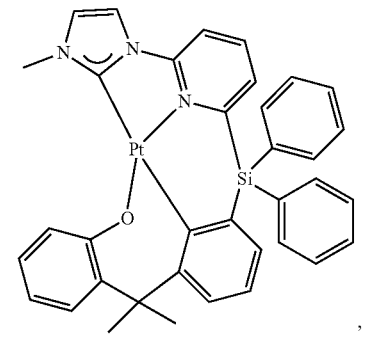
Compound 75
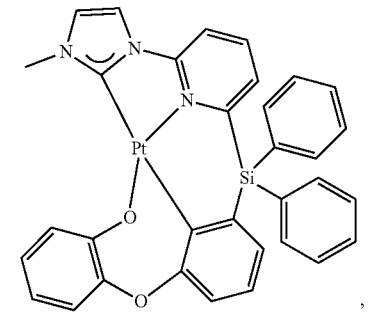
Compound 76
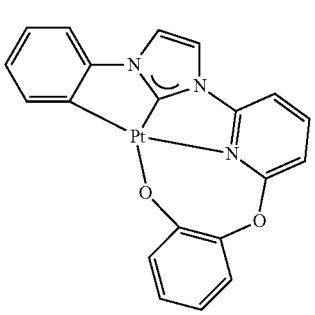
Compound 77
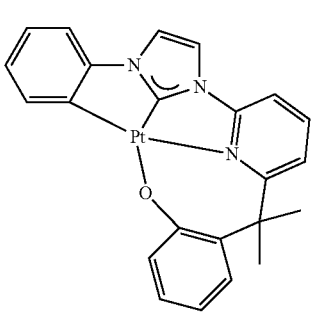
Compound 78
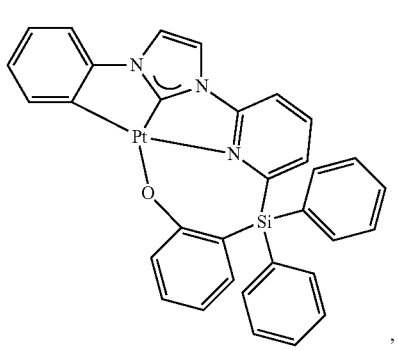
Compound 79
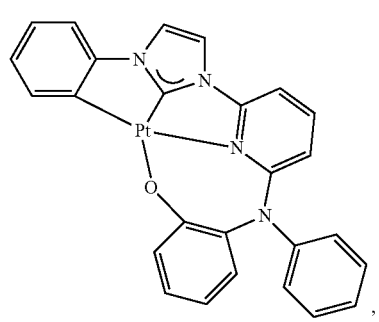
Compound 80
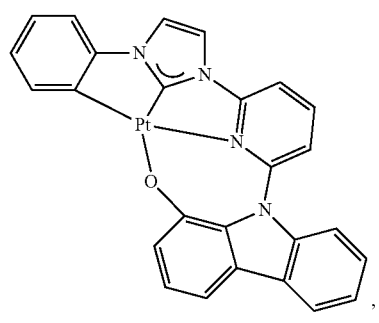

Compound 81
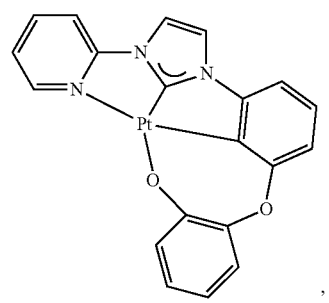
Compound 82
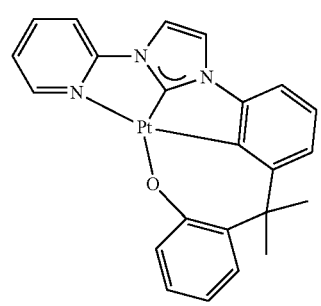
Compound 83
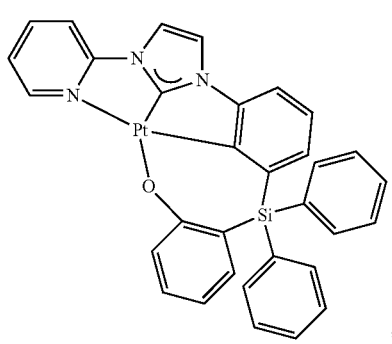
Compound 84
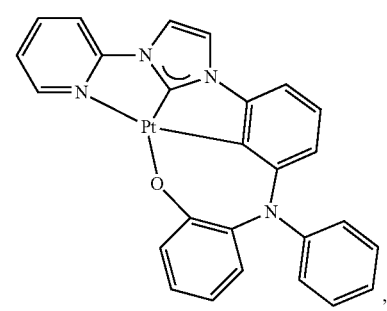
Compound 85
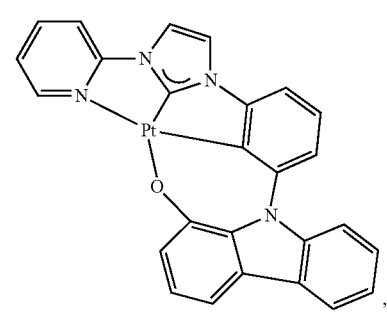
Compound 86
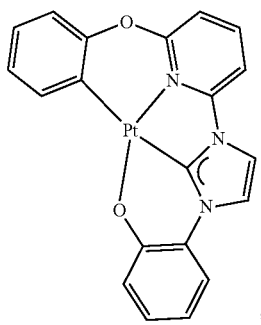
Compound 87
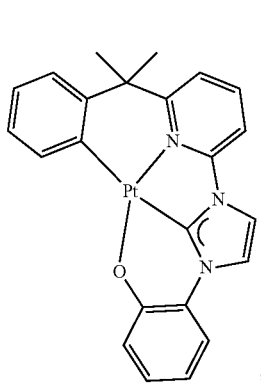
Compound 88
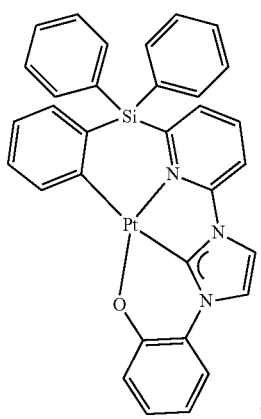
Compound 89
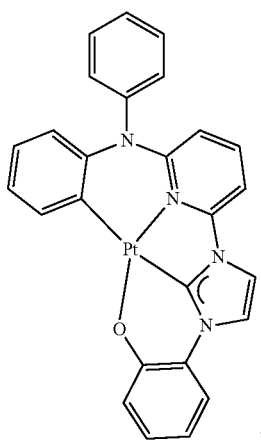

Compound 90
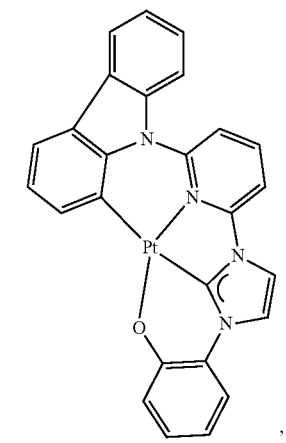
Compound 91
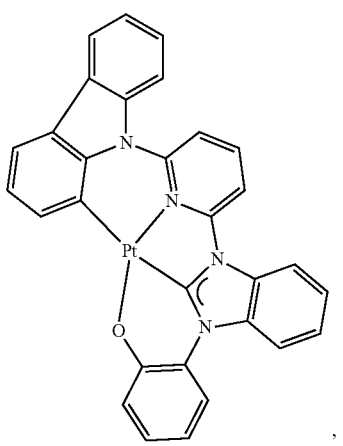
Compound 92
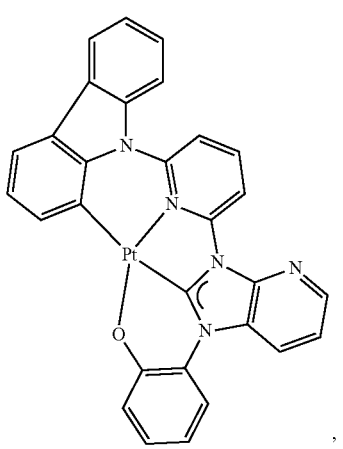
Compound 93
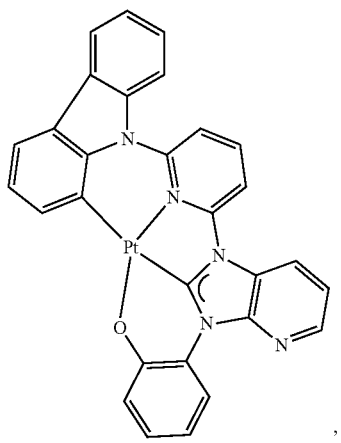
Compound 94
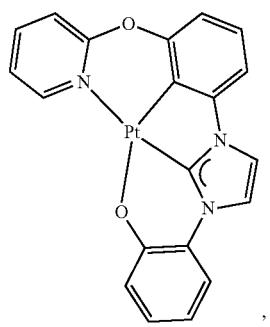
Compound 95
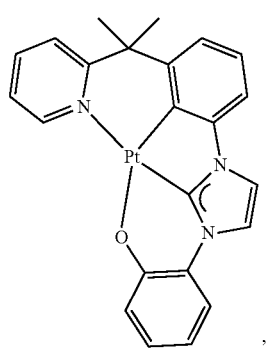
Compound 96
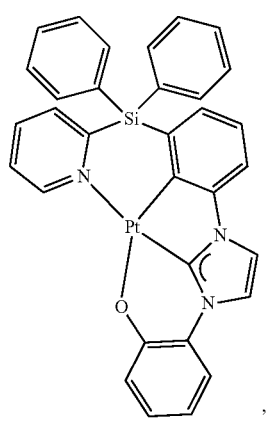

Compound 97
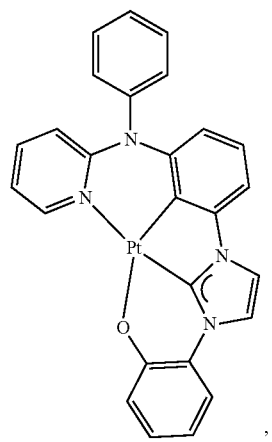
Compound 98
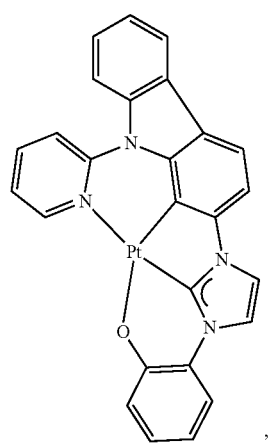
Compound 99
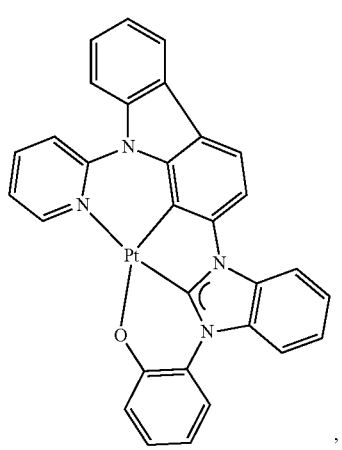
Compound 100
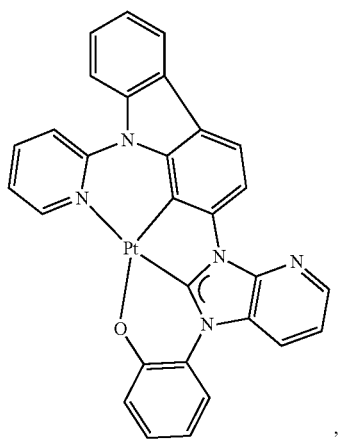
Compound 101
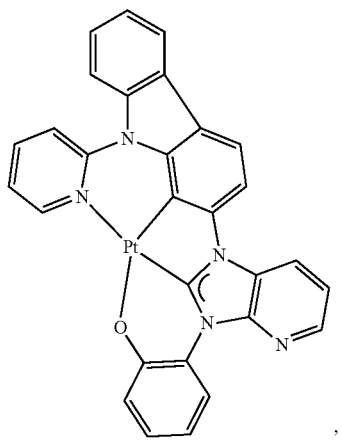
Compound 102
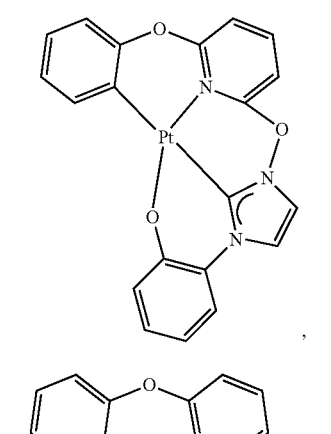
Compound 103
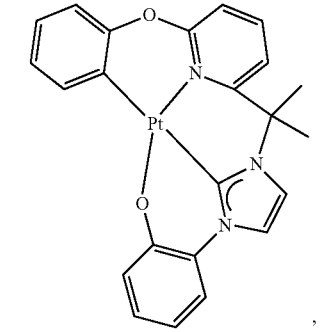

Compound 104
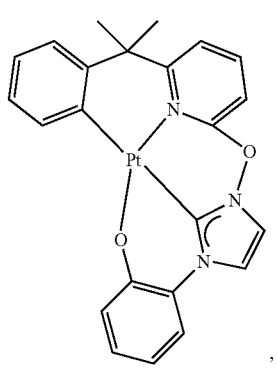
Compound 105
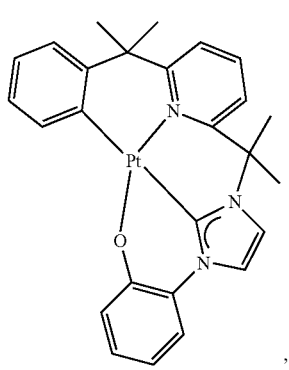
Compound 106
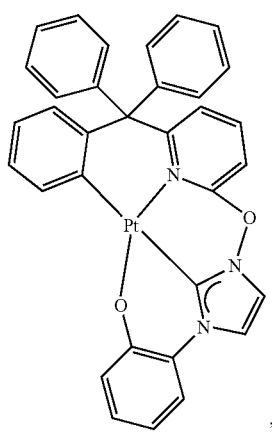
Compound 107
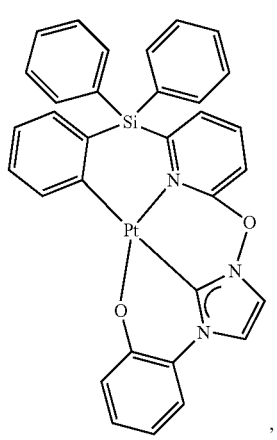
Compound 108
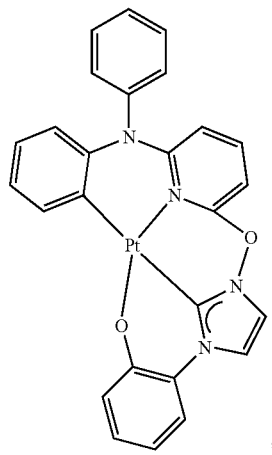
Compound 109
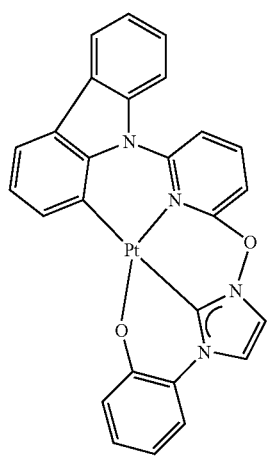
Compound 110
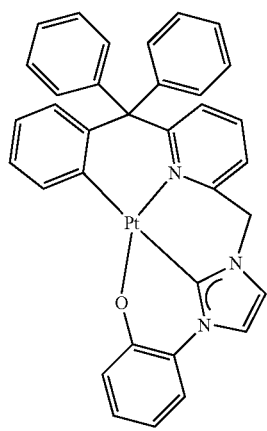

Compound 111
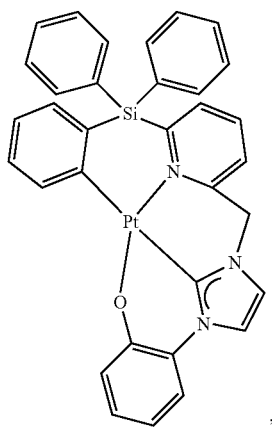
Compound 112
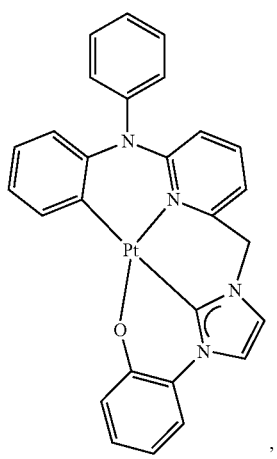
Compound 113
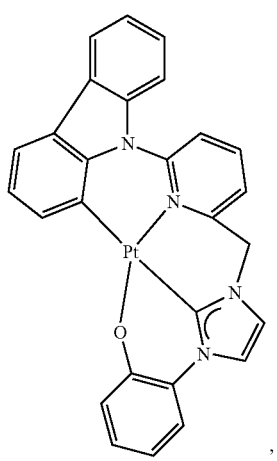
Compound 114
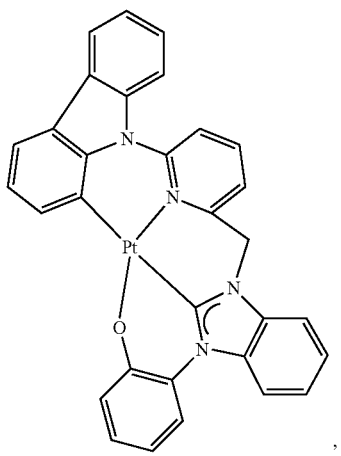
Compound 115
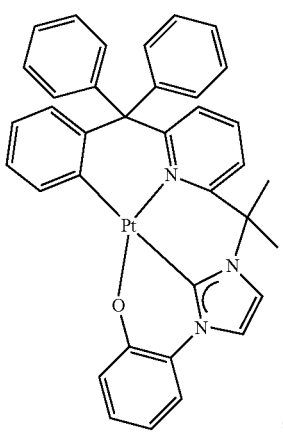
Compound 116
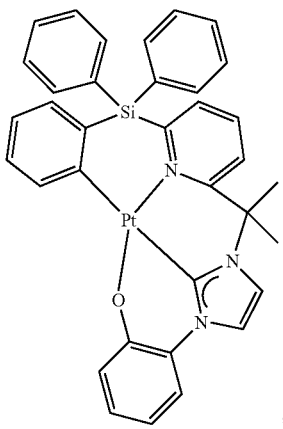

Compound 117
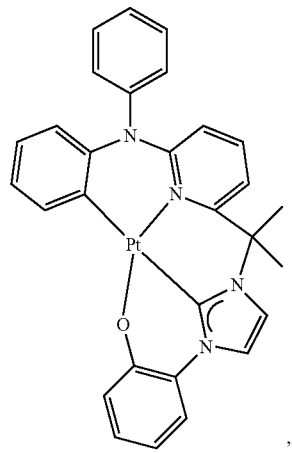
Compound 118
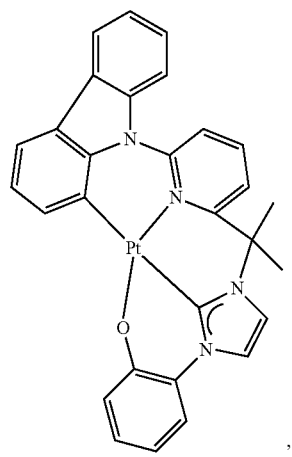
Compound 119
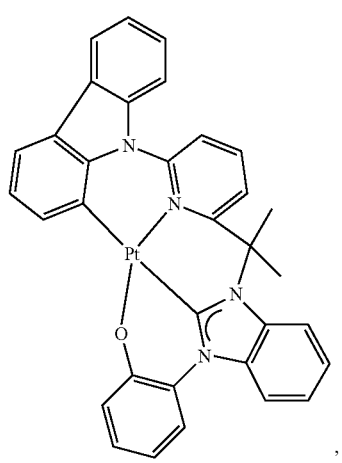
Compound 120
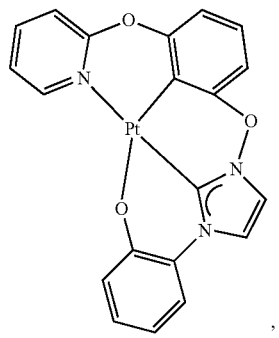
Compound 121
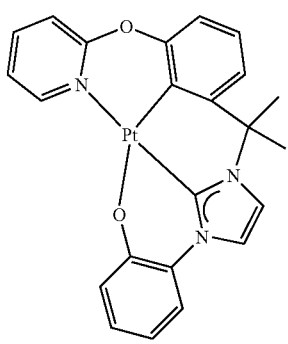
Compound 122
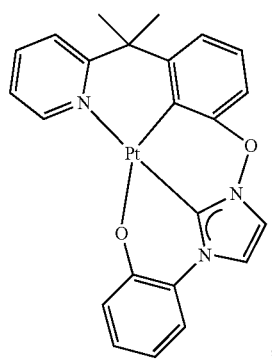
Compound 123
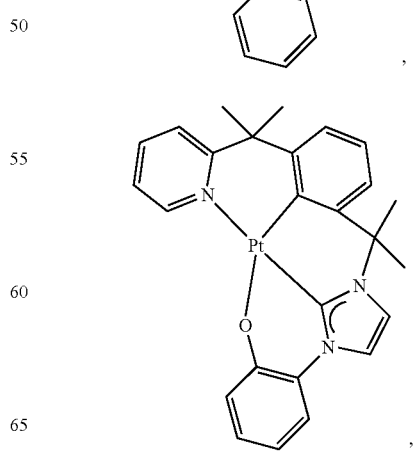

-continued
Compound 124
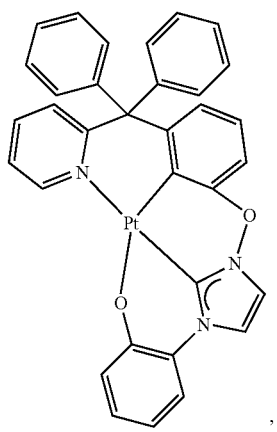
Compound 125
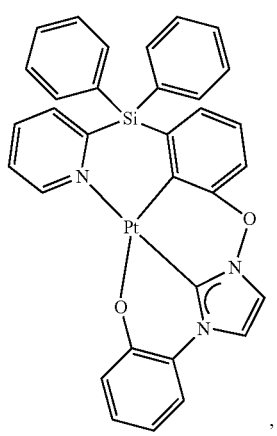
Compound 126
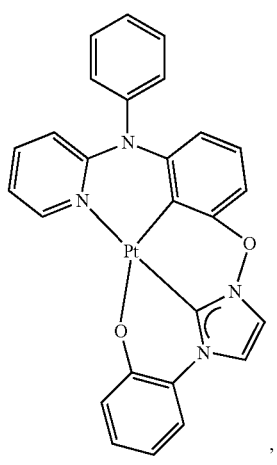
-continued
Compound 127
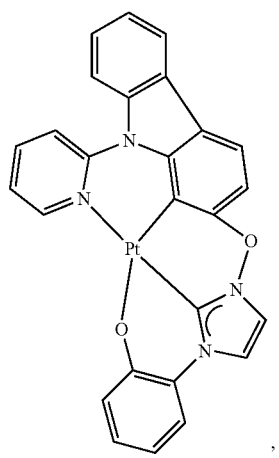
Compound 128
Compound 129
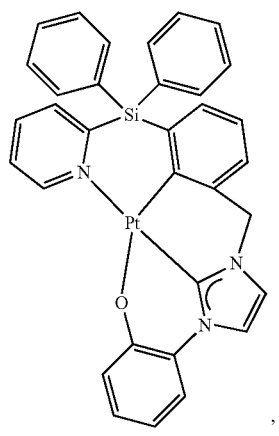

Compound 130
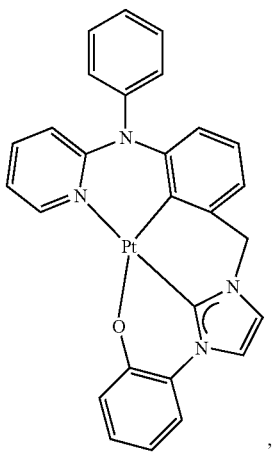
Compound 131
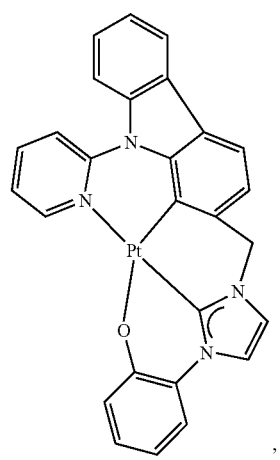
Compound 132
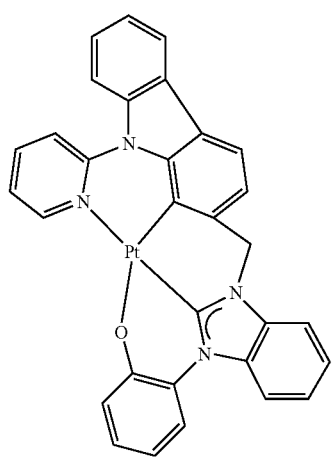
Compound 133
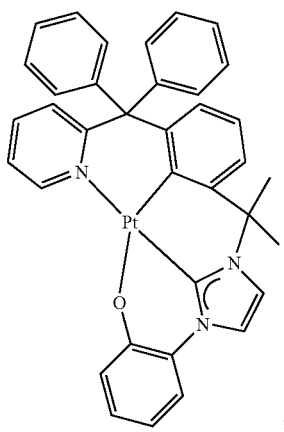
Compound 134
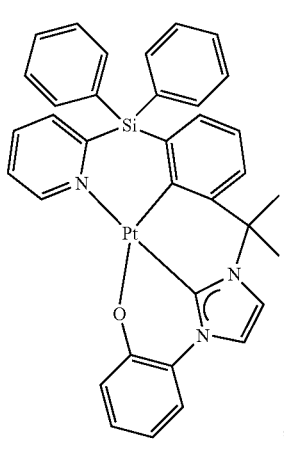
Compound 135
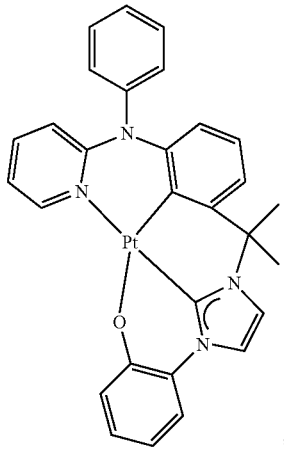

Compound 136

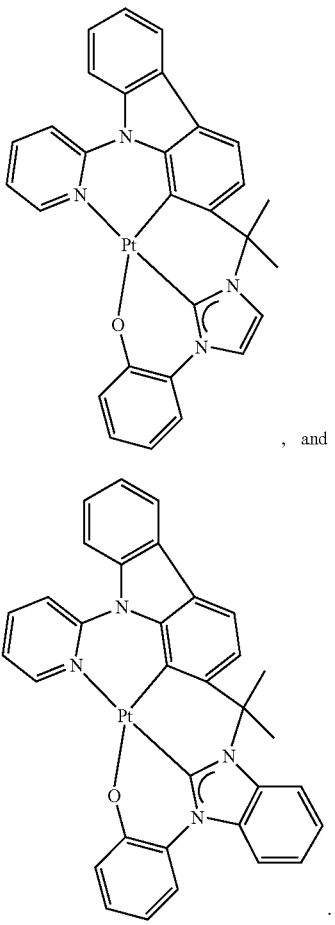

, and

Compound 137

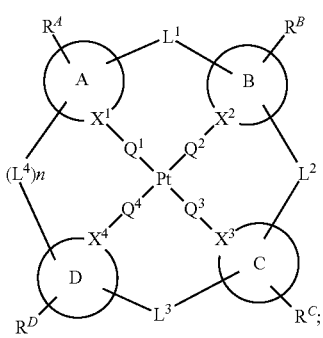

According to another aspect of the present disclosure, a device comprising one or more organic light emitting devices incorporating the compound disclosed herein is provided. At least one of the one or more organic light emitting devices comprise: an anode; a cathode; and an organic layer, disposed between the anode and the cathode, comprising a compound having a Pt tetradentate structure, having the formula:

Formula I wherein rings A, B, C, and D each independently represent a 5-membered or 6-membered carbocyclic or heterocyclic ring;
wherein $R^A$, $R^B$, $R^C$, and $R^D$ each independently represent mono, di, tri, or tetra-substitution, or no substitution;

wherein $L^1$, $L^2$, and $L^3$ are each independently selected from the group consisting of a direct bond, BR, NR, PR, O, S, Se, C=O, S=O, SO$_2$, CRR', SiRR', GeRR', and combinations thereof,
wherein when n is 1, $L^4$ is selected from the group consisting of a direct bond, BR, NR, PR, 0, S, Se, C=O, S=O, SO$_2$, CRR', SiRR', GeRR', and combinations thereof, when n is 0, $L^4$ is not present;
wherein $R^A$, $R^B$, $R^C$, $R^D$, R, and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof,
wherein any adjacent $R^A$, $R^B$, $R^C$, $R^D$, R, and R' are optionally joined to form a ring;
wherein $X^1$, $X^2$, $X^3$, and $X^4$ are each independently selected from the group consisting of carbon and nitrogen;
wherein one of $Q^1$, $Q^2$, $Q^3$, and $Q^4$ is oxygen, the remaining three of $Q^1$, $Q^2$, $Q^3$, and $Q^4$ each represent a direct bond so that Pt directly bonds to three of $X^1$, $X^2$, $X^3$, and $X^4$; and
wherein when $L^1$, $L^2$, $L^3$, or $L^4$ represents a direct bond, the direct bond is not a C—C bond.

In one embodiment of the device, the device is selected from the group consisting of a consumer product, an electronic component module, an organic light-emitting device, and a lighting panel.

In another embodiment of the device, the organic layer is an emissive layer and the compound is an emissive dopant or a non-emissive dopant.

In another embodiment of the device, the organic layer further comprises a host, wherein the host comprises a triphenylene containing benzo-fused thiophene or benzo-fused furan; wherein any substituent in the host is an unfused substituent independently selected from the group consisting of $C_mH_{2m+1}$, $OC_mH_{2m+1}$, $OAr_1$, $N(C_mH_{2m+1})_2$, $N(Ar_1)(Ar_2)$, CH=CH—$C_mH_{2m+1}$, C≡C$C_mH_{2m+1}$, $Ar_1$, $Ar_1$—$Ar_2$, $C_mH_{2m}$—$Ar_1$, or no substitution;
wherein m is from 1 to 10; and
wherein $Ar_1$ and $Ar_2$ are independently selected from the group consisting of benzene, biphenyl, naphthalene, triphenylene, carbazole, and heteroaromatic analogs thereof.

In some embodiments of the device, the organic layer further comprises a host, wherein the host comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

In one embodiment of the device, the host is selected from the group consisting of:

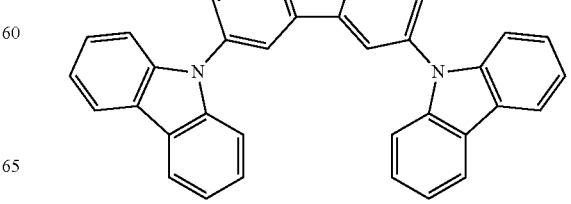

,

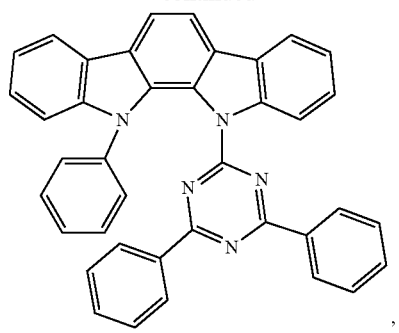
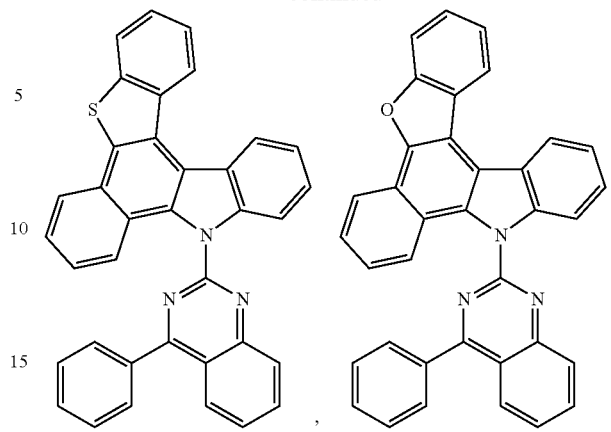
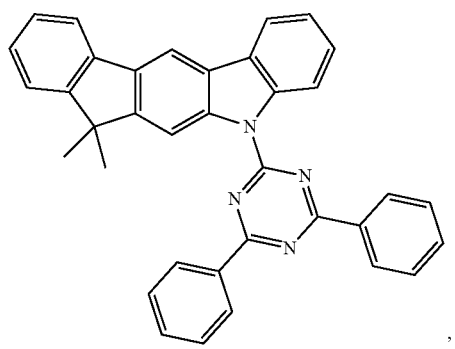
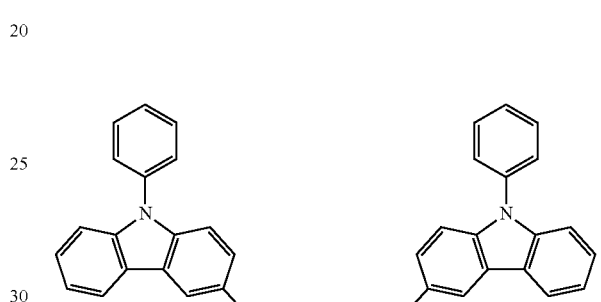
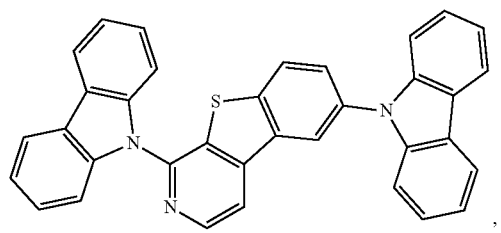
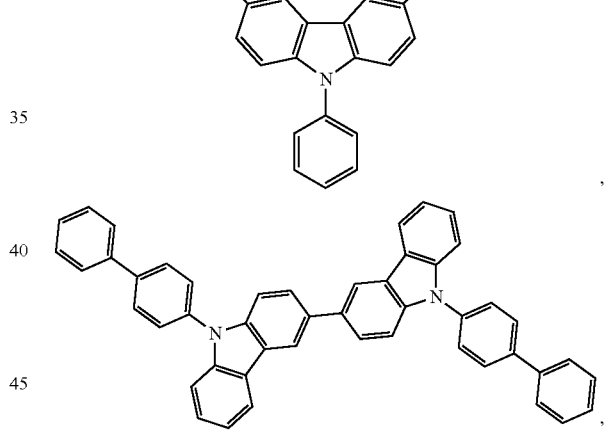
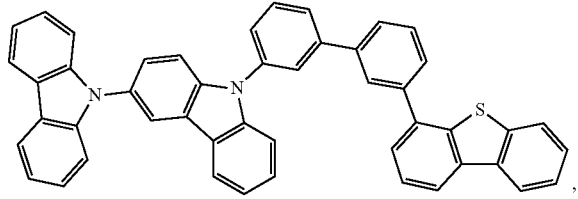
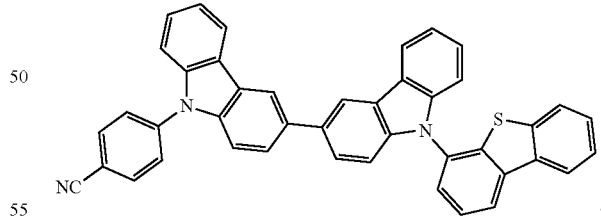
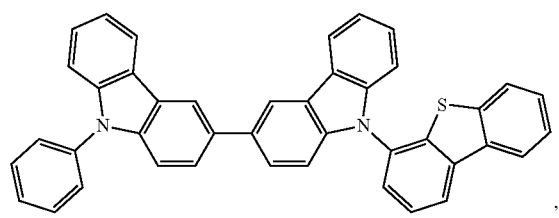
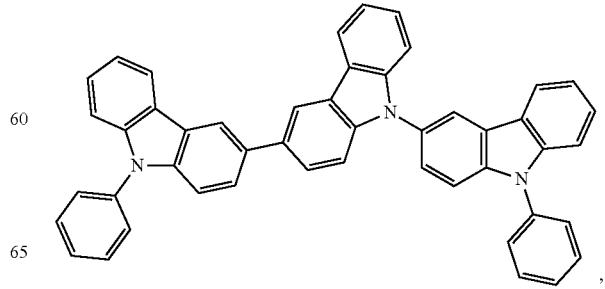
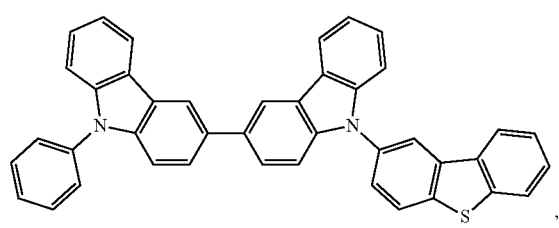

-continued

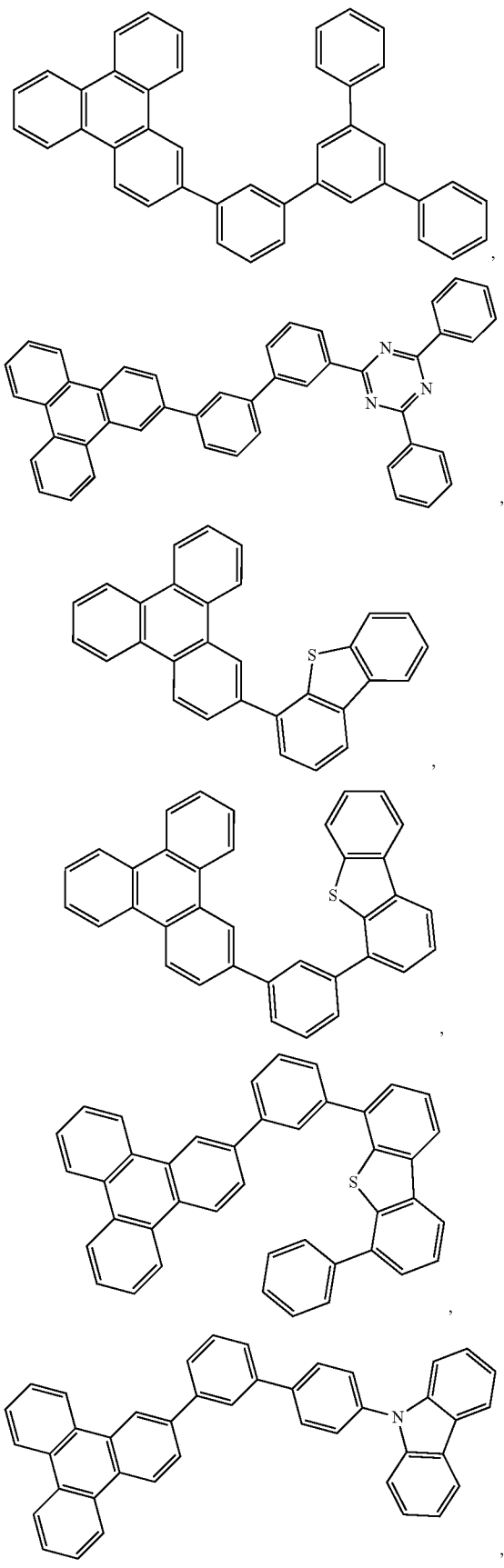

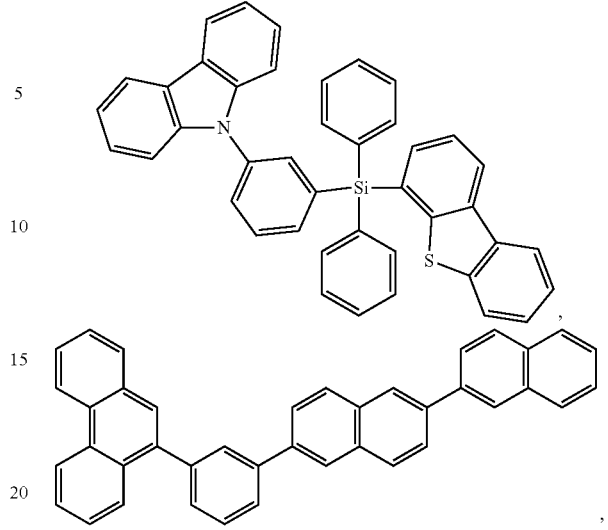

and combinations thereof.

In one embodiment of the device, the host comprises a metal complex.

According to another aspect of the present disclosure, a formulation comprising a compound having a Pt tetradentate structure, having Formula I as described herein including all variations thereof is disclosed.

According to another aspect of the present disclosure, a novel method for forming a metal-carbene bond is disclosed. The method is exemplified by the following scheme for synthesis of Compound 99:

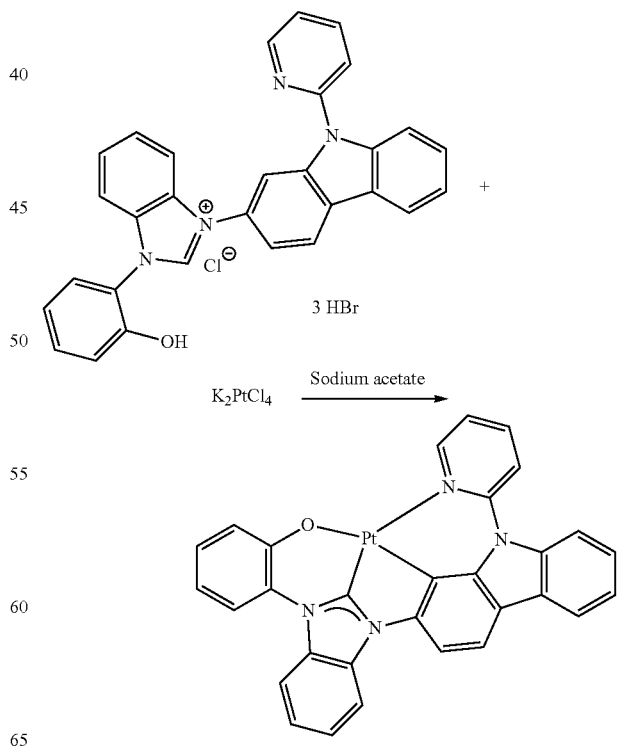

A 35 ml microwave reaction vessel was charged with a ligand

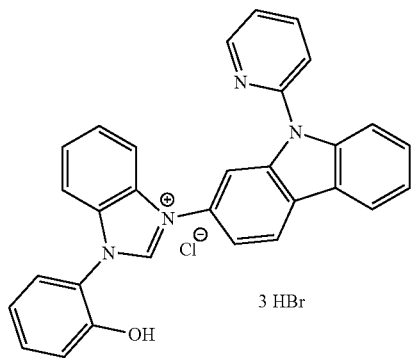 [SMILES: Oc1ccccc1-n1c[n+](-c2ccc3c4ccccc4n(-c4ccccn4)c3c2)c2ccccc21 ; [Cl-]]

(1 g, 1.367 mmol); $K_2PtCl_4$ (0.567 g, 1.367 mmol); sodium acetate (1.121 g, 13.67 mmol) and acetic acid (20 ml) forming a reaction mixture. The reaction mixture was heated in a microwave reactor (CEM brand; discovery model) to 160° C. for 10.5 hours. The reaction mixture was neutralized with aqueous ammonium and extracted by dichloromethane. The organic portion was combined and evaporated to dryness. The residue was subjected to column chromatography ($SiO_2$, $Et_3N$ pretreated, 100% dichloromethane) to yield the desired product (0.7 g, 79%).

The method comprises: mixing a metal precursor with a carbene salt, a weak base salt, and a solvent to form a reaction mixture; and heating the reaction mixture, wherein the weak base salt has pKa greater than 4.

N-heterocyclic carbenes (NHC) are one of the most promising new classes of ligands in the design of transition metal complexes. The general synthetic procedure is to carry out the deprotection of an imidazole salt followed by coordination of the resulting free carbene to the metal. However; this method usually requires cryogenic condition due to the short shelf life of the free carbene in ambient temperature. In this disclosure; we develop a methodology in which free carbene is not involved in the process. Therefore, cryogenic condition is not necessary and conventional heating process can be applied. This novel methodology shall be more practical in industrial setting environment. Furthermore, conventional carbene ligation is generally carried out in a basic or neutral condition due to high sensitivity of the free carbene toward acid. In the novel method of the present disclosure, since the free carbene is not involved in the process, the choice of the solvent is not restricted to a basic or neutral solvent. In fact, solvents with weak acidity can be used in the present method.

In one embodiment of the method, the metal precursor is a second or third row transition metal. In one embodiment, the metal precursor is selected from the group consisting of Ir, Rh, Re, Ru, Os, Pt, and Pd. In another embodiment, the metal precursor is a halide salt. In another embodiment, the metal precursor is selected from the group consisting of $K_2PtCl_4$, $Na_2PtCl_4$, $PtCl_2$, $PtCl_2(DMSO)_2$, $Pt(COD)Cl_2$, $IrCl_3 \cdot xH_2O$, $Na_2IrCl_6 \cdot xH_2O$, $(NH_4)_2IrCl_6$, $K_3IrCl_6 \cdot xH_2O$, $Na_2IrBr_6$, $[(COD)IrCl]_2$, $OsCl_3$ $xH_2O$, $(NH_4)_2OsCl_6$, $Na_2OsCl_6$, and $OsCl_2(DMSO)_2$.

In one embodiment of the method, the carbene salt is a carbon carbene salt. In another embodiment, the carbene salt is a N-heterocyclic carbene salt. In some embodiments, the carbene salt comprises a tetradentate ligand. In another embodiment, the carbene salt is a carbene halide salt.

In one embodiment of the method, the weak base salt is selected from the group consisting of: sodium acetate, potassium acetate, sodium butyrate, potassium butyrate, sodium propionate, and potassium propionate.

In one embodiment of the method, the solvent is the corresponding weak acid of the weak base salt. In some embodiments, the solvent is selected from the group consisting of acetic acid, propanoic acid, pivalic acid, and butyric acid.

In one embodiment of the method, the heating step is carried out in a microwave reactor.

In some embodiments of the method, the reaction mixture has a free carbene concentration of less than 10% of the carbene salt concentration. In one embodiment, the reaction mixture has a free carbene concentration of less than 1% of the carbene salt concentration. In one embodiment, the reaction mixture has a free carbene concentration of less than 0.1% of the carbene salt concentration.

In some embodiments of the method, the method produces a metal-carbene complex having a yield of at least 50%. In one embodiment, the method produces a metal-carbene complex having a yield of at least 70%.

In yet another aspect of the present disclosure, a formulation comprising a compound of Formula I as defined herein including all of their variations, is provided. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compound.

Examples of aromatic amine derivatives used in HIL or HTL include, but are not limited to the following general structures:

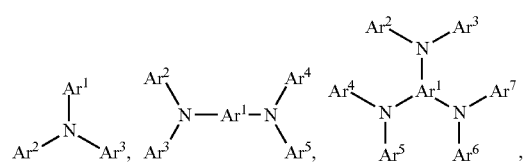

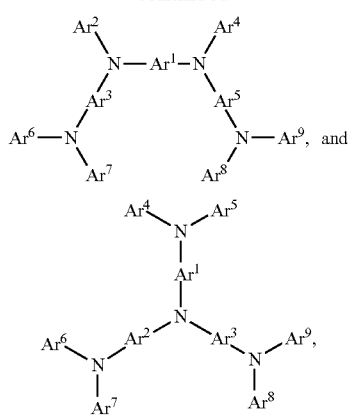

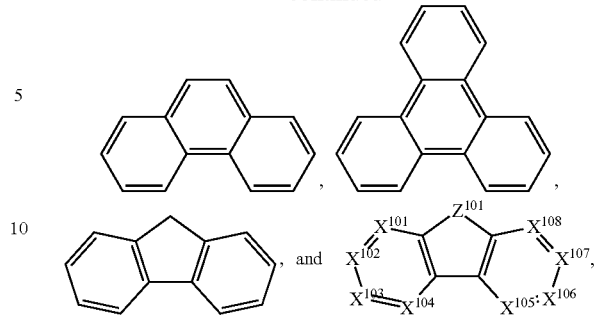

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of

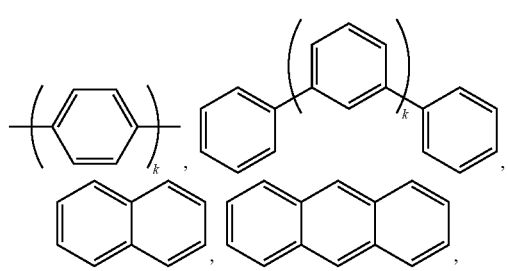

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

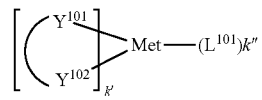

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+$/Fc couple less than about 0.6 V.
Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

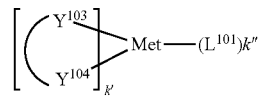

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

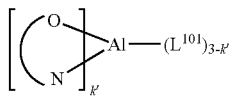 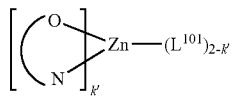

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of organic compounds used as host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

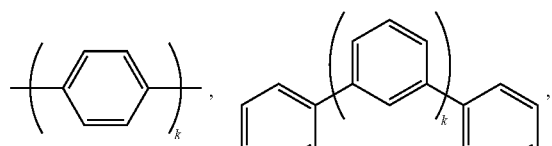

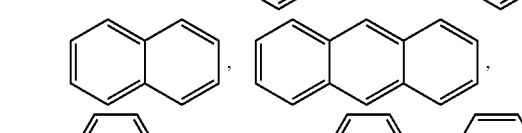

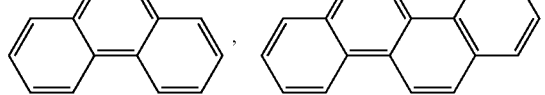

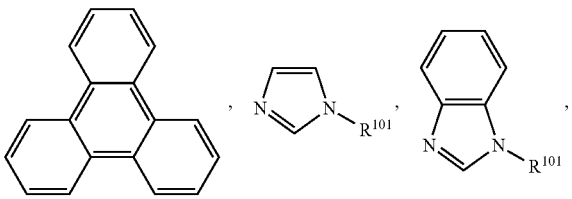

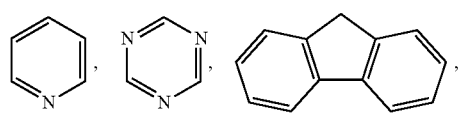

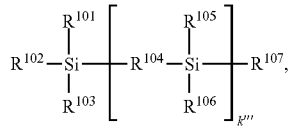

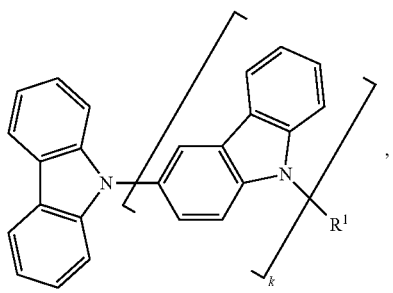

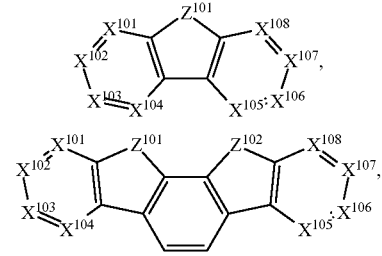

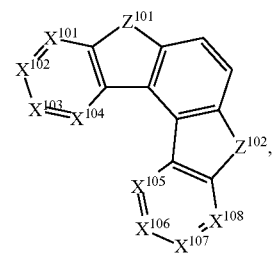

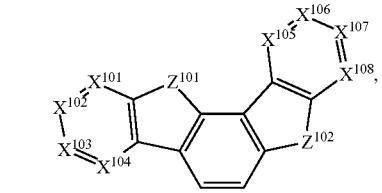

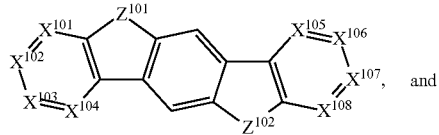

and

-continued

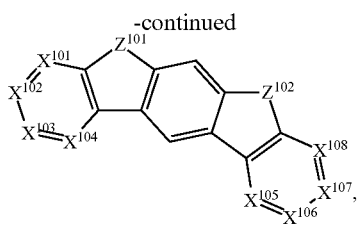

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

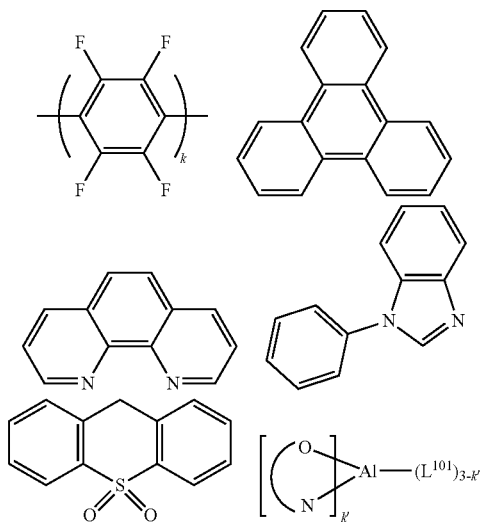

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

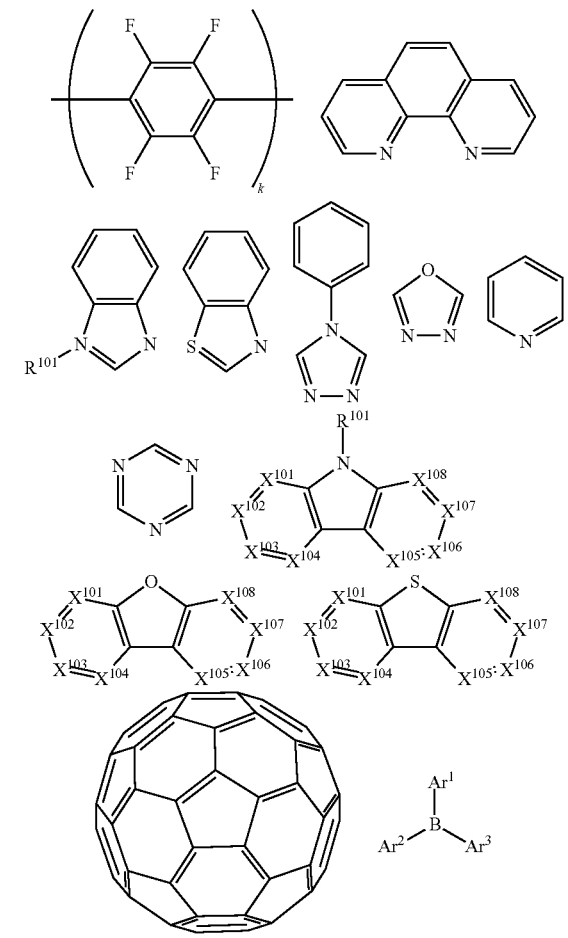

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

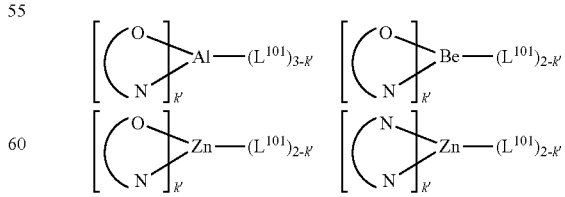

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A

| MATERIAL | EXAMPLES OF MATERIAL | PUBLICATIONS |
|---|---|---|
| Hole injection materials | | |
| Phthalocyanine and porphyrin compounds | 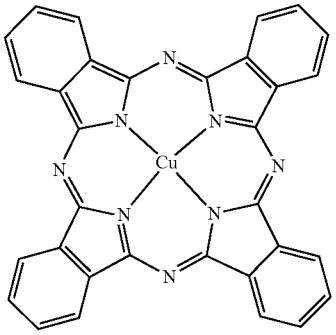 | Appl. Phys. Lett. 69, 2160 (1996) |
| Starburst triarylamines | 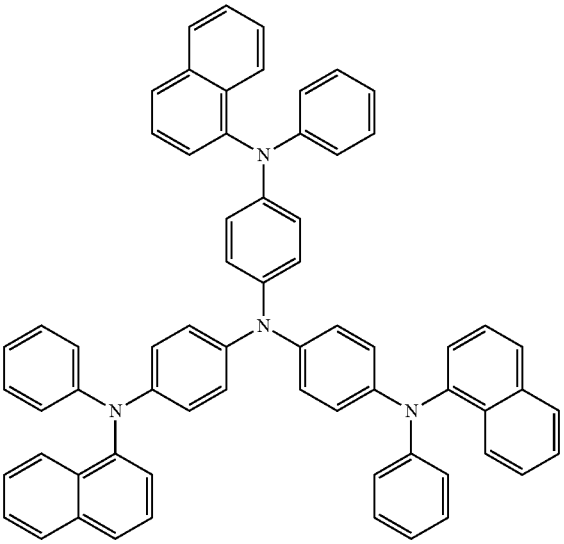 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | 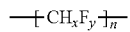 | Appl. Phys. Lett. 78, 673 (2001) |
| Conducting polymers (e.g., PEDOT:PSS, polyaniline, polythiophene) | 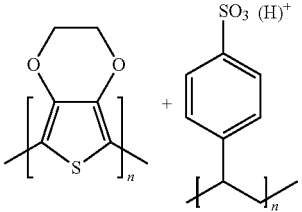 | Synth. Met. 87, 171 (1997) WO2007002683 |
| Phosphonic acid and silane SAMs | 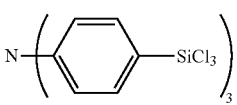 | US20030162053 |

TABLE A-continued
| MATERIAL | EXAMPLES OF MATERIAL | PUBLICATIONS |
|---|---|---|
| Triarylamine or polythiophene polymers with conductivity dopants | 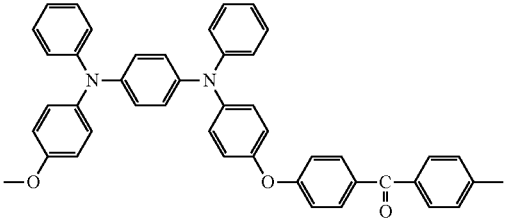 and 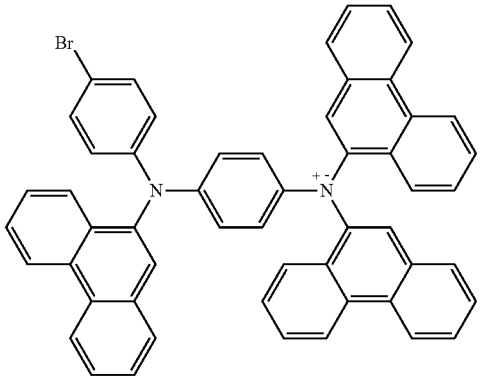 [SMILES: Brc1ccc(N(c2ccc(N(c3cc4ccccc4c4ccccc34)c3cc4ccccc4c4ccccc34)cc2)c2cc3ccccc3c3ccccc23)cc1] 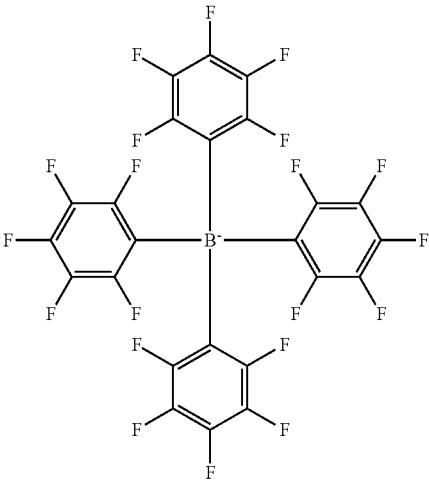 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Organic compounds with conductive inorganic compounds, such as molybdenum and tungsten oxides | 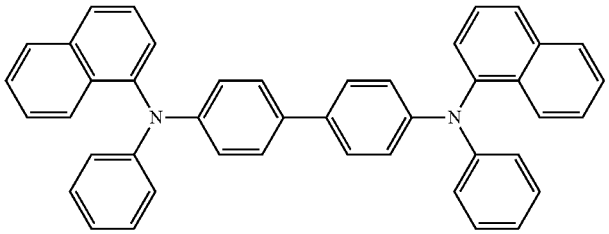 + MoO$_x$ | US20050123751 SID Symposium Digest, 37, 923 (2006) WO2009018009 |

TABLE A-continued
| MATERIAL | EXAMPLES OF MATERIAL | PUBLICATIONS |
| --- | --- | --- |
| n-type semiconducting organic complexes | 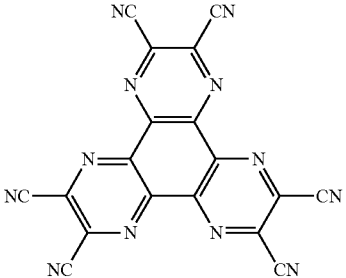 [SMILES: N#Cc1nc2c3nc(C#N)c(C#N)nc3c3nc(C#N)c(C#N)nc3c2nc1C#N] | US20020158242 |
| Metal organometallic complexes | 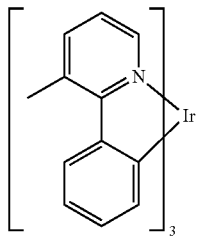 | US20060240279 |
| Cross-linkable compounds | 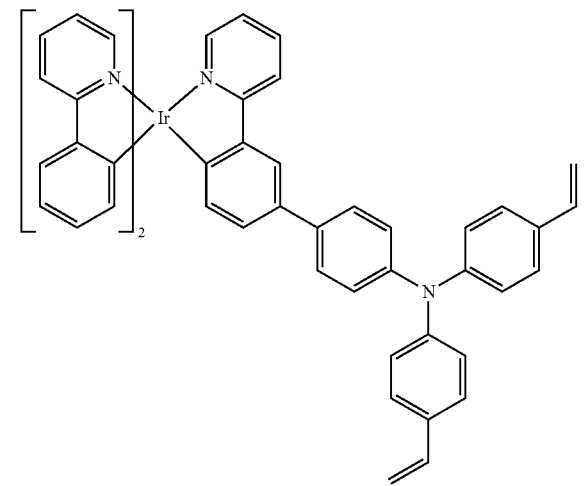 | US20080220265 |
| Polythiophene based polymers and copolymers | 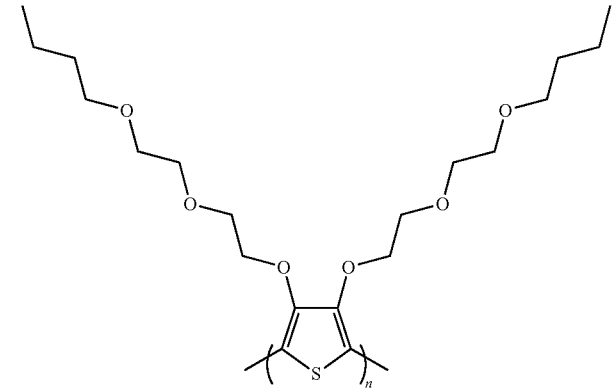 | WO 2011075644<br>EP2350216 |
| Hole transporting materials | | |

TABLE A-continued
| MATERIAL | EXAMPLES OF MATERIAL | PUBLICATIONS |
|---|---|---|
| Triarylamines (e.g., TPD, □-NPD) | 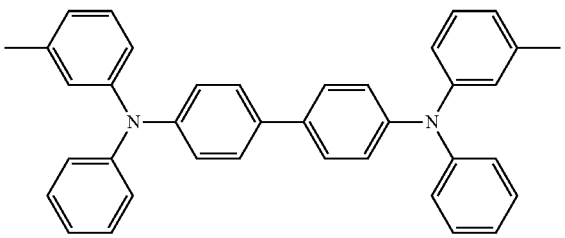 | Appl. Phys. Lett. 51, 913 (1987) |
| | 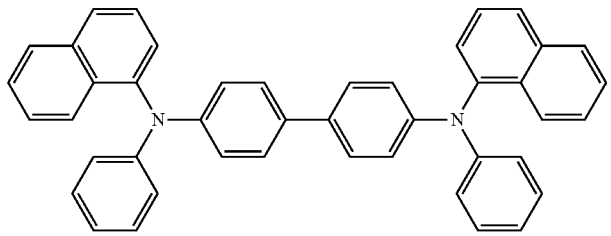 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 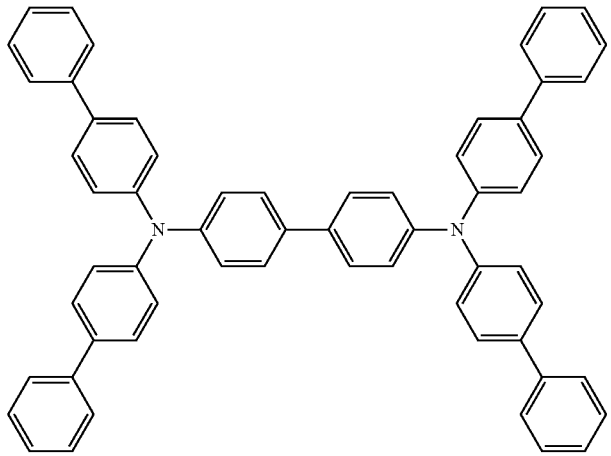 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 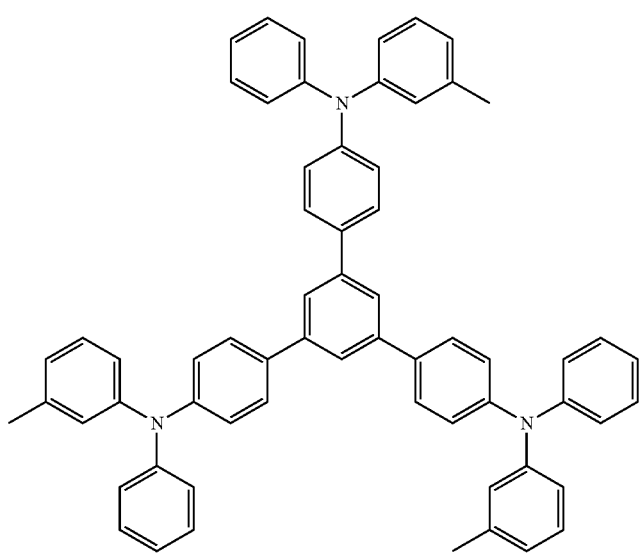 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE A-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US20080124572 |

TABLE A-continued
| MATERIAL | EXAMPLES OF MATERIAL | PUBLICATIONS |
|---|---|---|
| Triarylamine with (di)benzothiophene/(di)benzofuran | 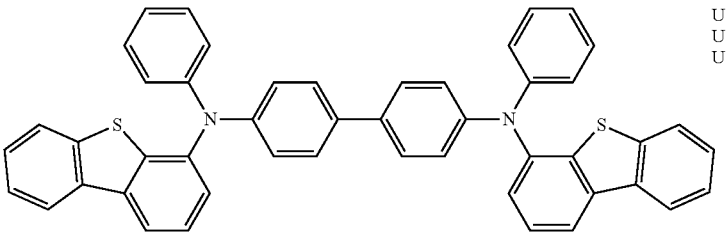 | US20070278938, US20080106190 US20110163302 |
| Indolocarbazoles | 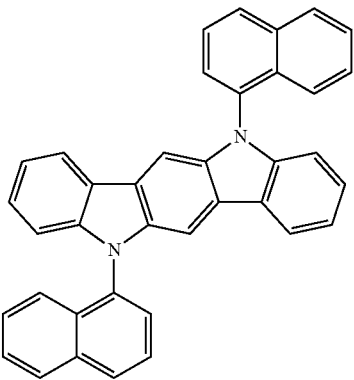 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 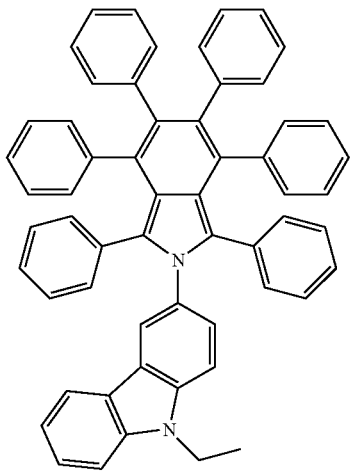 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 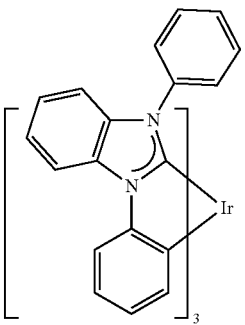 | US20080018221 |

TABLE A-continued

| MATERIAL | EXAMPLES OF MATERIAL | PUBLICATIONS |
|---|---|---|
| Phosphorescent OLED host materials | | |
| Red hosts | | |
| Arylcarbazoles | | Appl. Phys. Lett. 78, 1622 (2001) |
| Metal 8-hydroxyquinolates (e.g., $Alq_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE A-continued

| MATERIAL | EXAMPLES OF MATERIAL | PUBLICATIONS |
| --- | --- | --- |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |
| Green hosts | | |
| Arylcarbazoles | | Appl. Phys. Lett. 78, 1622 (2001) |
| | | US20030175553 |
| | | WO2001039234 |

TABLE A-continued
| MATERIAL | EXAMPLES OF MATERIAL | PUBLICATIONS |
|---|---|---|
| Aryltriphenylene compounds | 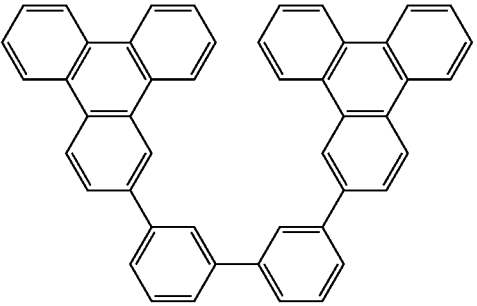 [SMILES: c1cc(-c2cccc(-c3ccc4c5ccccc5c5ccccc5c4c3)c2)cc(-c2ccc3c4ccccc4c4ccccc4c3c2)c1] | US20060280965 |
|  | 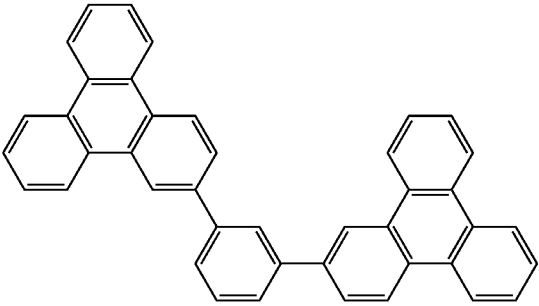 [SMILES: c1cc(-c2ccc3c4ccccc4c4ccccc4c3c2)cc(-c2ccc3c4ccccc4c4ccccc4c3c2)c1] | US20060280965 |
|  | 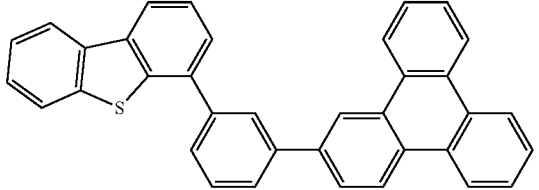 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 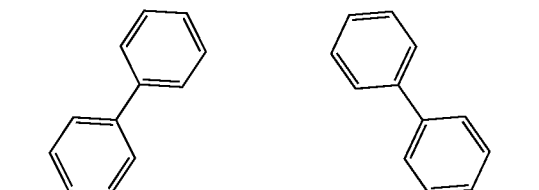 | US20090309488<br>US20090302743<br>US20100012931 |
| Donor acceptor type molecules | 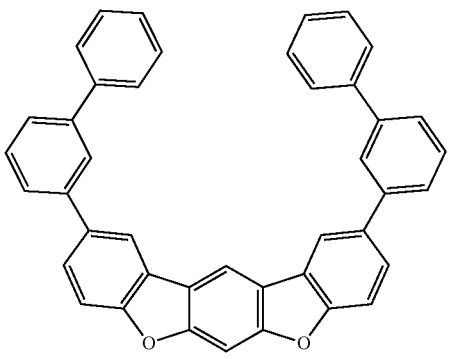 [SMILES: c1ccc(-c2cccc(-c3ccc4oc5cc6oc7ccc(-c8cccc(-c9ccccc9)c8)cc7c6cc5c4c3)c2)cc1] | WO2008056746 |

TABLE A-continued

| MATERIAL | EXAMPLES OF MATERIAL | PUBLICATIONS |
| --- | --- | --- |
| | | WO2010107244 |
| Aza-carbazole/DBT/DBF | | JP2008074939 |
| | | US20100187984 |
| Polymers (e.g., PVK) | | Appl. Phys. Lett. 77, 2280 (2000) |
| Spirofluorene compounds | | WO2004093207 |

TABLE A-continued

| MATERIAL | EXAMPLES OF MATERIAL | PUBLICATIONS |
| --- | --- | --- |
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE A-continued

| MATERIAL | EXAMPLES OF MATERIAL | PUBLICATIONS |
| --- | --- | --- |
| Indolocarbazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE A-continued

| MATERIAL | EXAMPLES OF MATERIAL | PUBLICATIONS |
| --- | --- | --- |
| Metal phenoxypyridine compounds | | WO2005030900 |
| Metal coordination complexes (e.g., Zn, Al with N^N ligands) | | US20040137268, US20040137267 |
| Blue hosts | | |
| Arylcarbazoles | | Appl. Phys. Lett, 82, 2422 (2003) |
| | | US20070190359 |
| Dibenzothiophene/ Dibenzofuran- carbazole compounds | | WO2006114966, US20090167162 |
| | | US20090167162 |

TABLE A-continued
| MATERIAL | EXAMPLES OF MATERIAL | PUBLICATIONS |
|---|---|---|
| | 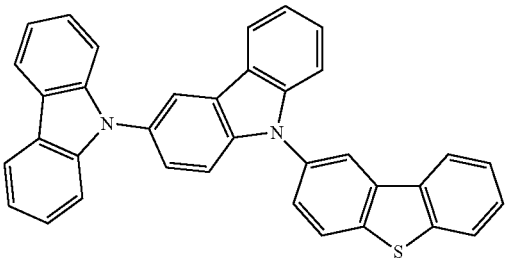 [SMILES: c1ccc2c(c1)sc1ccc(-n3c4ccccc4c4cc(-n5c6ccccc6c6ccccc65)ccc43)cc12] | WO2009086028 |
| | 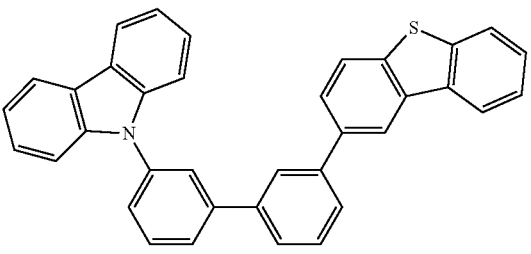 [SMILES: c1cc(-c2cccc(-n3c4ccccc4c4ccccc43)c2)cc(-c2ccc3sc4ccccc4c3c2)c1] | US20090030202, US20090017330 |
| | 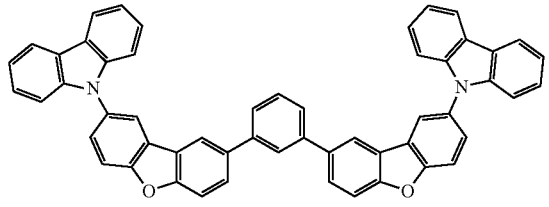 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 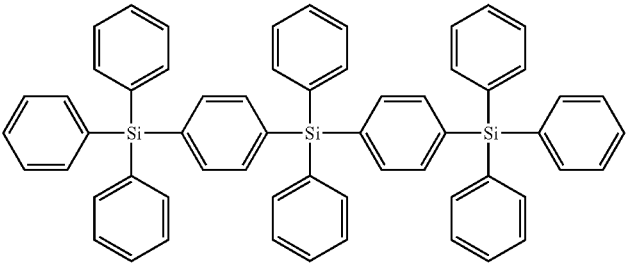 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 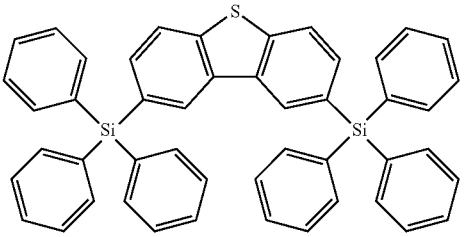 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 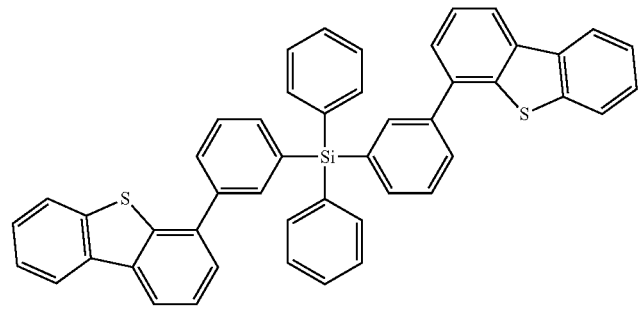 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |

TABLE A-continued

| MATERIAL | EXAMPLES OF MATERIAL | PUBLICATIONS |
| --- | --- | --- |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S. Pat. No. 7,154,114 |
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |

TABLE A-continued

| MATERIAL | EXAMPLES OF MATERIAL | PUBLICATIONS |
|---|---|---|
| | | US20030072964 |
| | | US20030072964 |
| | | US20060202194 |
| | | US20060202194 |
| | | US20070087321 |

TABLE A-continued

| MATERIAL | EXAMPLES OF MATERIAL | PUBLICATIONS |
|---|---|---|
| | | US20080261076<br>US20100090591 |
| | | US20070087321 |
| | | Adv. Mater. 19, 739 (2007) |
| | | WO2009100991 |
| | | WO2008101842 |

TABLE A-continued
| MATERIAL | EXAMPLES OF MATERIAL | PUBLICATIONS |
|---|---|---|
| | 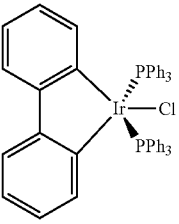 | U.S. Pat. No. 7,232,618 |
| Platinum(II) organometallic complexes | 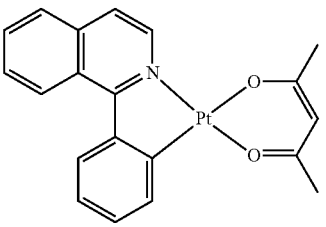 | WO2003040257 |
| | 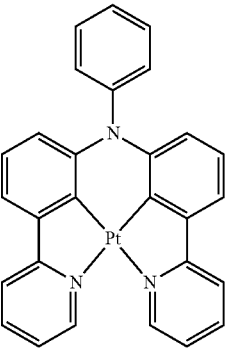 | US20070103060 |
| Osmium(III) complexes | 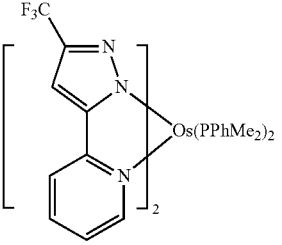 | Chem. Mater. 17, 3532 (2005) |
| Ruthenium(II) complexes | 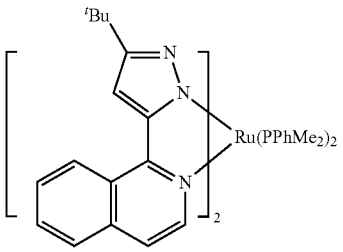 | Adv. Mater. 17, 1059 (2005) |
| Rhenium (I), (II), and (III) complexes | 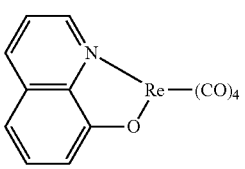 | US20050244673 |

TABLE A-continued
| MATERIAL | EXAMPLES OF MATERIAL | PUBLICATIONS |
|---|---|---|
| Green dopants | | |
| Iridium(III) organometallic complexes | 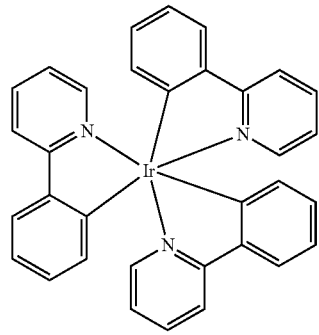 and its derivatives | Inorg. Chem. 40, 1704 (2001) |
| | 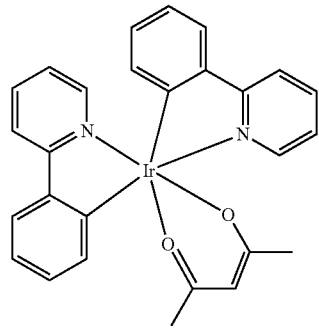 | US20020034656 |
| | 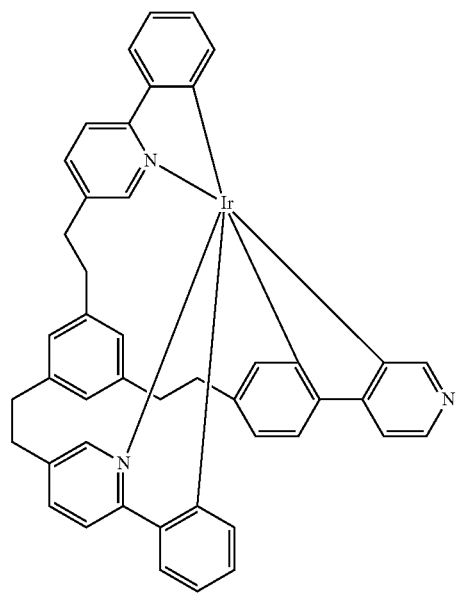 | U.S. Pat. No. 7,332,232 |

TABLE A-continued
| MATERIAL | EXAMPLES OF MATERIAL | PUBLICATIONS |
|---|---|---|
| | 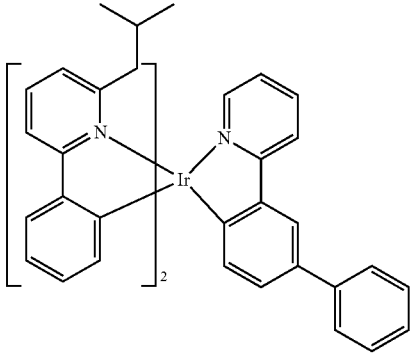 | US20090108737 |
| | 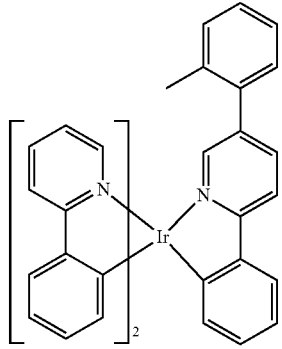 | WO2010028151 |
| | 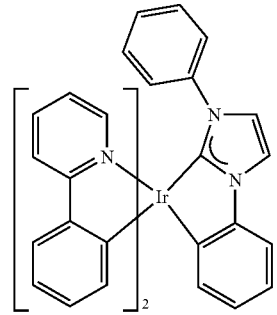 | EP1841834B |
| | 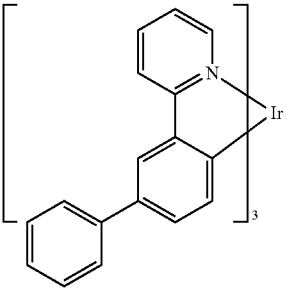 | US20060127696 |
| | 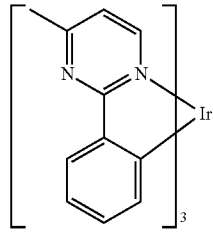 | US20090039776 |

TABLE A-continued

| MATERIAL | EXAMPLES OF MATERIAL | PUBLICATIONS |
| --- | --- | --- |
| | | U.S. Pat. No. 6,921,915 |
| | | US20100244004 |
| | | U.S. Pat. No. 6,687,266 |
| | | Chem. Mater. 16, 2480 (2004) |
| | | US20070190359 |

TABLE A-continued

| MATERIAL | EXAMPLES OF MATERIAL | PUBLICATIONS |
|---|---|---|
| | | US 20060008670
JP2007123392 |
| | | WO2010086089,
WO2011044988 |
| | | Adv. Mater. 16, 2003
(2004) |
| | | Angew. Chem. Int. Ed.
2006, 45, 7800 |
| | | WO2009050290 |
| | | US20090165846 |

TABLE A-continued
| MATERIAL | EXAMPLES OF MATERIAL | PUBLICATIONS |
|---|---|---|
| | 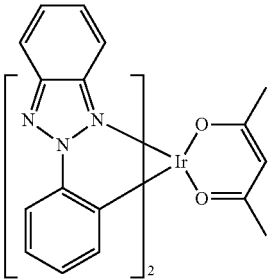 | US20080015355 |
| | 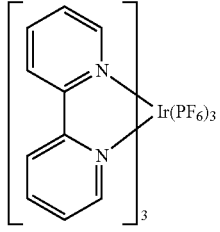 | US20010015432 |
| | 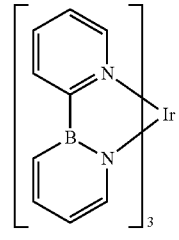 | US20100295032 |
| Monomer for polymeric metal organometallic compounds | 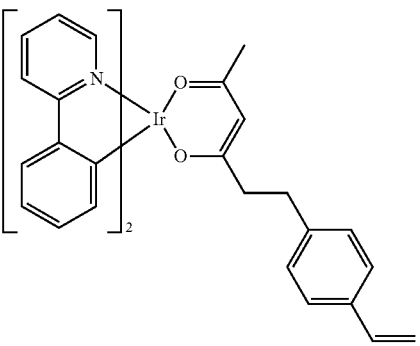 | U.S. Pat. No. 7,250,226, U.S. Pat. No. 7,396,598 |
| Pt(II) organometallic complexes, including polydentated ligands | 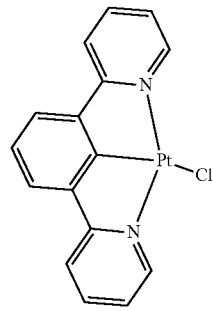 | Appl. Phys. Lett. 86, 153505 (2005) |

TABLE A-continued
| MATERIAL | EXAMPLES OF MATERIAL | PUBLICATIONS |
|---|---|---|
| | 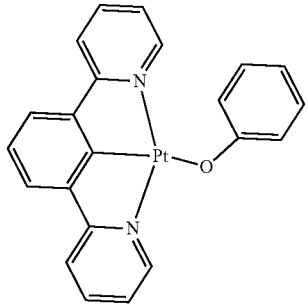 | Appl. Phys. Lett. 86, 153505 (2005) |
| | 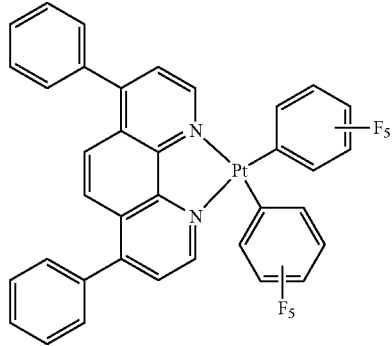 | Chem. Lett. 34, 592 (2005) |
| | 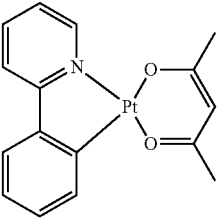 | WO2002015645 |
| | 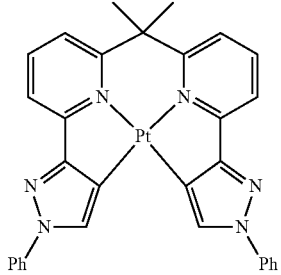 | US20060263635 |
| | 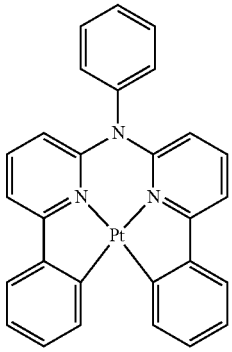 | US20060182992<br>US20070103060 |

TABLE A-continued
| MATERIAL | EXAMPLES OF MATERIAL | PUBLICATIONS |
|---|---|---|
| Cu complexes | 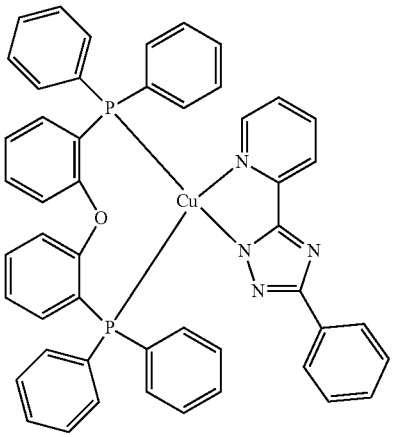 | WO2009000673 |
|  | 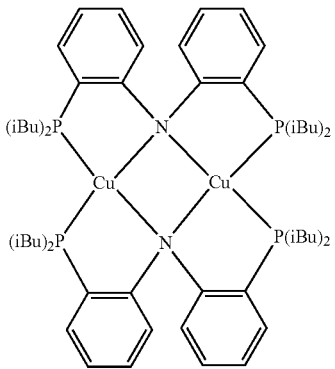 | US20070111026 |
| Gold complexes | 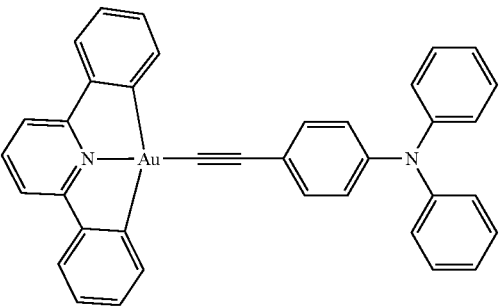 | Chem. Commun. 2906 (2005) |
| Rhenium(III) complexes | 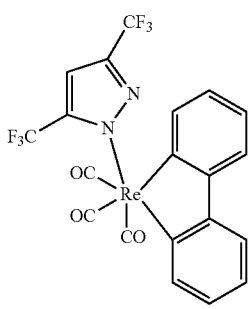 | Inorg. Chem. 42, 1248 (2003) |

TABLE A-continued

| MATERIAL | EXAMPLES OF MATERIAL | PUBLICATIONS |
| --- | --- | --- |
| Osmium(II) complexes | | U.S. Pat. No. 7,279,704 |
| Deuterated organometallic complexes | | US20030138657 |
| Organometallic complexes with two or more metal centers | | US20030152802 |
| | | U.S. Pat. No. 7,090,928 |

TABLE A-continued

| MATERIAL | EXAMPLES OF MATERIAL | PUBLICATIONS |
| --- | --- | --- |
| Blue dopants | | |
| Iridium(III) organometallic complexes | | WO2002002714 |
| | | WO2006009024 |
| | | US20060251923<br>US20110057559<br>US20110204333 |
| | | U.S. Pat. No. 7,393,599,<br>WO2006056418,<br>US20050260441,<br>WO2005019373 |
| | | U.S. Pat. No. 7,534,505 |

TABLE A-continued

| MATERIAL | EXAMPLES OF MATERIAL | PUBLICATIONS |
|---|---|---|
| | | WO2011051404 |
| | | U.S. Pat. No. 7,445,855 |
| | | US20070190359, US20080297033 US20100148663 |
| | | U.S. Pat. No. 7,338,722 |
| | | US20020134984 |

TABLE A-continued
| MATERIAL | EXAMPLES OF MATERIAL | PUBLICATIONS |
|---|---|---|
| | 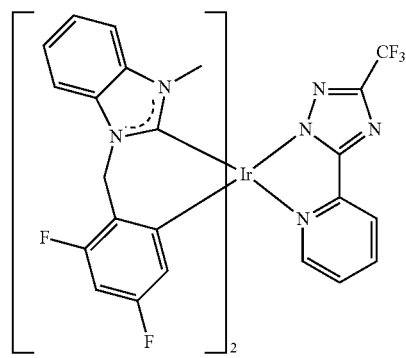 | Angew. Chem. Int. Ed. 47, 4542 (2008) |
| | 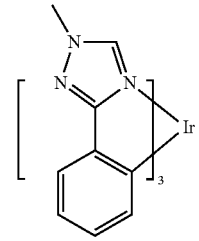 | Chem. Mater. 18, 5119 (2006) |
| | 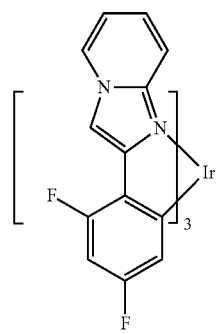 | Inorg. Chem. 46, 4308 (2007) |
| | 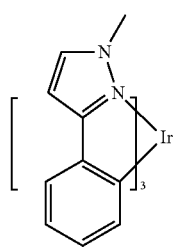 | WO2005123873 |
| | 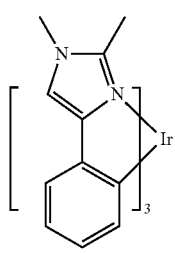 | WO2005123873 |

TABLE A-continued
| MATERIAL | EXAMPLES OF MATERIAL | PUBLICATIONS |
|---|---|---|
| | 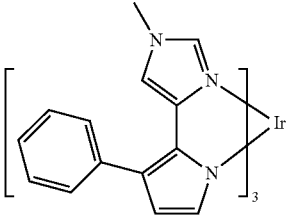 | WO2007004380 |
| | 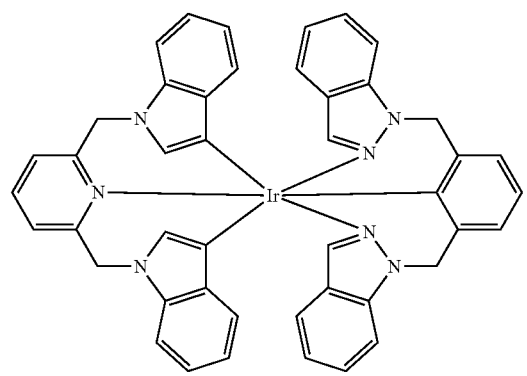 | WO2006082742 |
| Osmium(II) complexes | 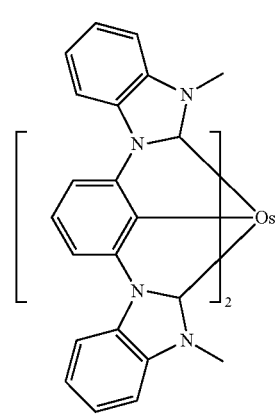 | U.S. Pat. No. 7,279,704 |
| | 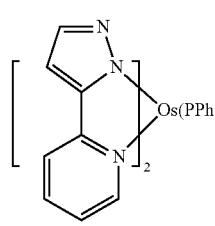 | Organometallics 23, 3745 (2004) |
| Gold complexes | 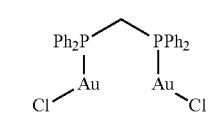 | Appl. Phys. Lett. 74, 1361 (1999) |
| Platinum(II) complexes | 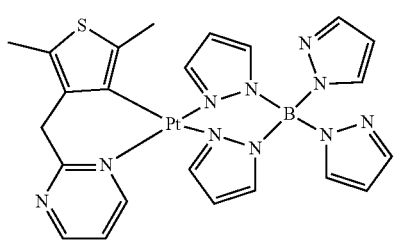 | WO2006098120, WO2006103874 |

TABLE A-continued

| MATERIAL | EXAMPLES OF MATERIAL | PUBLICATIONS |
| --- | --- | --- |
| Pt tetradentate complexes with at least one metal-carbene bond | | U.S. Pat. No. 7,655,323 |
| Exciton/hole blocking layer materials | | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

TABLE A-continued

| MATERIAL | EXAMPLES OF MATERIAL | PUBLICATIONS |
| --- | --- | --- |
| Triphenylene compounds | | US20050025993 |
| Fluorinated aromatic compounds | | Appl. Phys. Lett. 79, 156 (2001) |
| Phenothiazine-S-oxide | | WO2008132085 |
| Silylated five-membered nitrogen, oxygen, sulfur or phosphorus dibenzoheterocycles | | WO2010079051 |

TABLE A-continued

| MATERIAL | EXAMPLES OF MATERIAL | PUBLICATIONS |
| --- | --- | --- |
| Aza-carbazoles | | US20060121308 |
| Electron transporting materials | | |
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |

TABLE A-continued

| MATERIAL | EXAMPLES OF MATERIAL | PUBLICATIONS |
| --- | --- | --- |
| Metal 8-hydroxyquinolates (e.g., $Alq_3$, $Zrq_4$) | | Appl. Phys. Lett. 51, 913 (1987)<br>U.S. Pat. No. 7,230,107 |
| Metal hydroxybenzoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |

TABLE A-continued

| MATERIAL | EXAMPLES OF MATERIAL | PUBLICATIONS |
| --- | --- | --- |
|  |  | Jpn. J. Apply. Phys. 32, L917 (1993) |
| Silole compounds |  | Org. Electron. 4, 113 (2003) |
| Arylborane compounds |  | J. Am. Chem. Soc. 120, 9714 (1998) |
| Fluorinated aromatic compounds |  | J. Am. Chem. Soc. 122, 1832 (2000) |
| Fullerene (e.g., C60) |  | US20090101870 |
| Triazine complexes |  | US20040036077 |

TABLE A-continued

| MATERIAL | EXAMPLES OF MATERIAL | PUBLICATIONS |
|---|---|---|
| Zn (N^N) complexes | 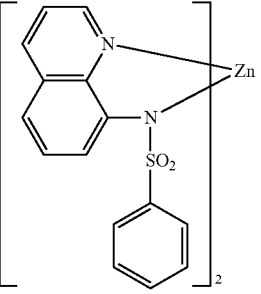 | U.S. Pat. No. 6,528,187 |

EXPERIMENTAL

Synthesis of Compound 99

Synthesis of 2-methoxy-N-(2-nitrophenyl) aniline

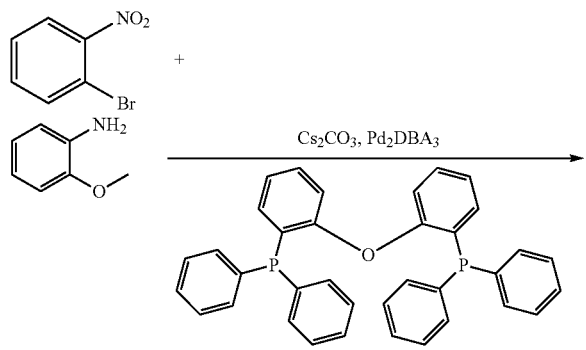

A three neck 500 ml round bottom flask was charged with 1-bromo-2-nitrobenzene (10 g, 49.5 mmol); 2-methoxyaniline (5.58 ml, 49.5 mmol); Cs$_2$CO$_3$ (47.4 g, 146 mmol); (oxybis(2,1-phenylene))bis(diphenylphosphine) (1.920 g, 3.56 mmol); Pd$_2$dba$_3$ (1.088 g, 1.188 mmol), and toluene (250 ml). The reaction mixture was refluxed for 17 hours. The reaction was then filtered through a pad of Celite®. The organic layer was combined and subjected to column chromatography (SiO$_2$, 5% THF in heptane) to yield 2-methoxy-N-(2-nitrophenyl)aniline (11.55 g, 96%).

Synthesis of N1-(2-methoxyphenyl)benzene-1,2-diamine

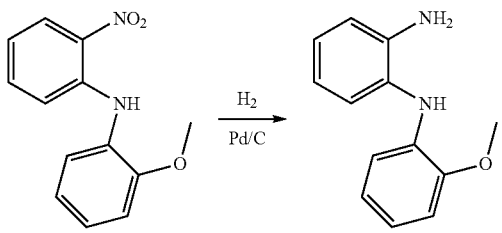 [SMILES: COc1ccccc1Nc1ccccc1[N+](=O)[O-] ; "H2" ; COc1ccccc1Nc1ccccc1N]

A 500 ml hydrogenation bottle was charged with 2-methoxy-N-(2-nitrophenyl)aniline (11.55 g, 47.3 mmol); 10% pd/c (0.75 g) and EtOH (200 ml). The reaction was shaken under 50 psi of H$_2$ for 4 hours. The reaction mixture was filtered through a pad of Celite®. The organic portion was subjected to column chromatography (SiO$_2$, 10% THF in heptane) to yield N1-(2-methoxyphenyl)benzene-1,2-diamine (8.67 g, 86%).

Synthesis of N1-(2-methoxyphenyl)-N2-(9-(pyridin-2-yl)-9H-carbazol-2-yl)benzene-1,2-diamine

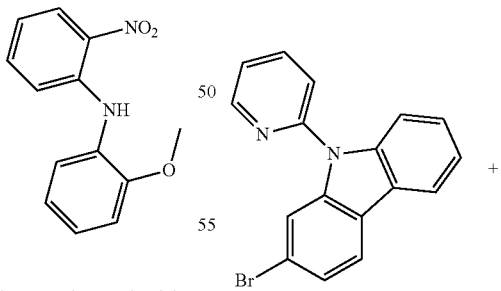

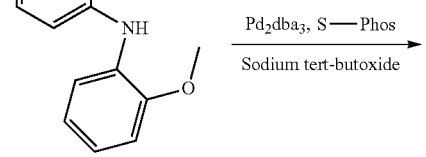

-continued

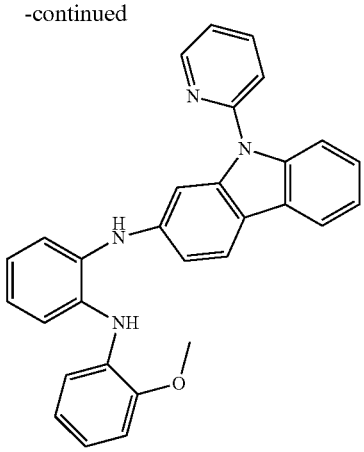

A 500 ml three neck round bottom flask was charged with 2-bromo-9-(pyridin-2-yl)-9H-carbazole (10.24 g, 31.7 mmol); N1-(2-methoxyphenyl)benzene-1,2-diamine (6.79 g, 31.7 mmol); Pd$_2$dba$_3$ (0.870 g, 0.951 mmol); dicyclohexyl (2',6'-dimethoxy-[1,1'-biphenyl]-2-yl)phosphine (S-Phos) (1.561 g, 3.80 mmol); sodium t-butoxide (5.12 g, 53.2 mmol) and 150 ml of anhydrous toluene. The reaction was heated to reflux for 17 hours. The reaction mixture was then diluted with saturated ammonium chloride solution and extracted with ethyl acetate. The organic portion was combined and evaporated to dryness. The residue was subjected to column chromatography (SiO$_2$, 20% THF in heptane) to yield N1-(2-methoxyphenyl)-N2-(9-(pyridin-2-yl)-9H-carbazol-2-yl)benzene-1,2-diamine (12.24 g, 85%).

Synthesis of 3-(2-methoxyphenyl)-1-(9-(pyridin-2-yl)-9H-carbazol-2-yl)-1H-benzo[d]imidazol-3-ium chloride

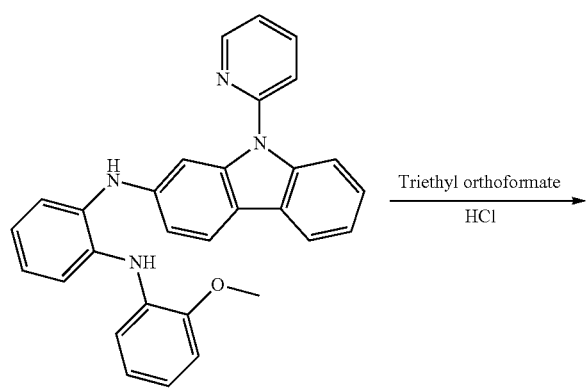

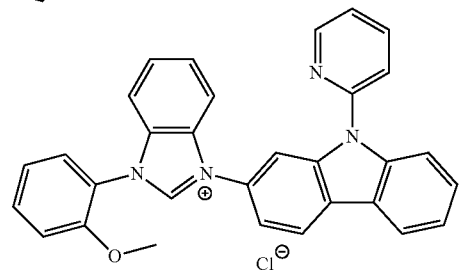

A 500 ml round bottom flask was charged with N1-(2-methoxyphenyl)-N2-(9-(pyridin-2-yl)-9H-carbazol-2-yl)benzene-1,2-diamine (12.24 g, 26.8 mmol), triethylorthoformate (150 ml); 4 ml of concentrated HCl and 10 drops of formic acid. The reaction was reflux for 6 hours. The reaction mixture was filtered and yield 3-(2-methoxyphenyl)-1-(9-(pyridin-2-yl)-9H-carbazol-2-yl)-1H-benzo[d]imidazol-3-ium chloride. (12 g, 89%).

Synthesis of ligand for Compound 99

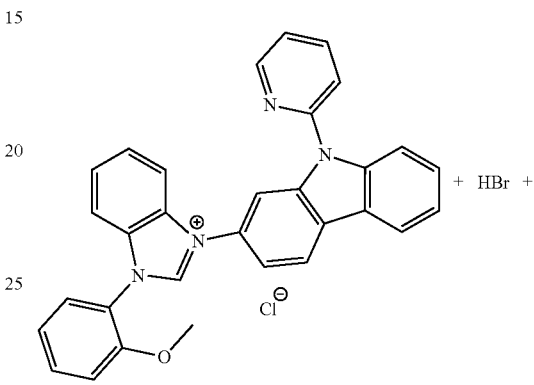

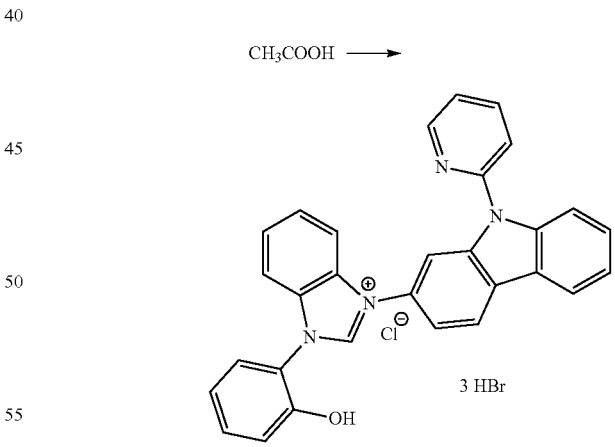

A 35 ml microwave reactor vessel was charged with 3-(2-methoxyphenyl)-1-(9-(pyridin-2-yl)-9H-carbazol-2-yl)-1H-benzo[d]imidazol-3-ium chloride (3 g, 5.96 mmol) and 12 ml of solution (HBr:HOAC=1:1 by volume). The reaction mixture was subjected to microwave reactor (CEM brand; discovery model) and heated to 140° C. for 1.5 hours. The reaction mixture was filtered and the precipitation was washed with acetone to yield the desired ligand. (3.8 g, 88%).

Synthesis of Compound 99

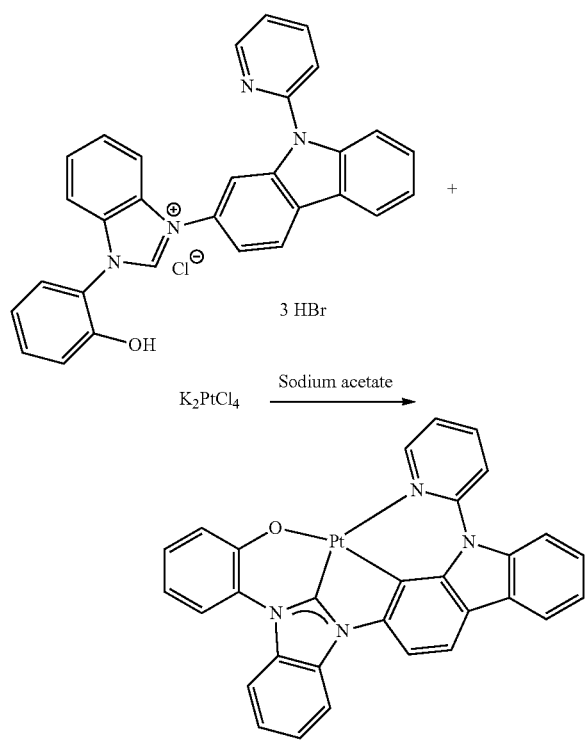

A 35 ml microwave reaction vessel was charged with ligand (1 g, 1.367 mmol), $K_2PtCl_4$ (0.567 g, 1.367 mmol), sodium acetate (1.121 g, 13.67 mmol), and acetic acid (20 ml). The reaction mixture was subjected to microwave reactor (CEM brand; discovery model) and heated to 160° C. for 10.5 hours. The reaction mixture was neutralized with aqueous ammonium and extracted by dichloromethane. The organic portion was combined and evaporated to dryness. The residue was subjected to column chromatography ($SiO_2$, triethylamine pretreated, 100% dichloromethane) to yield Compound 99 (0.7 g, 79%).

Photophysics of Compound 99

Figure 4:
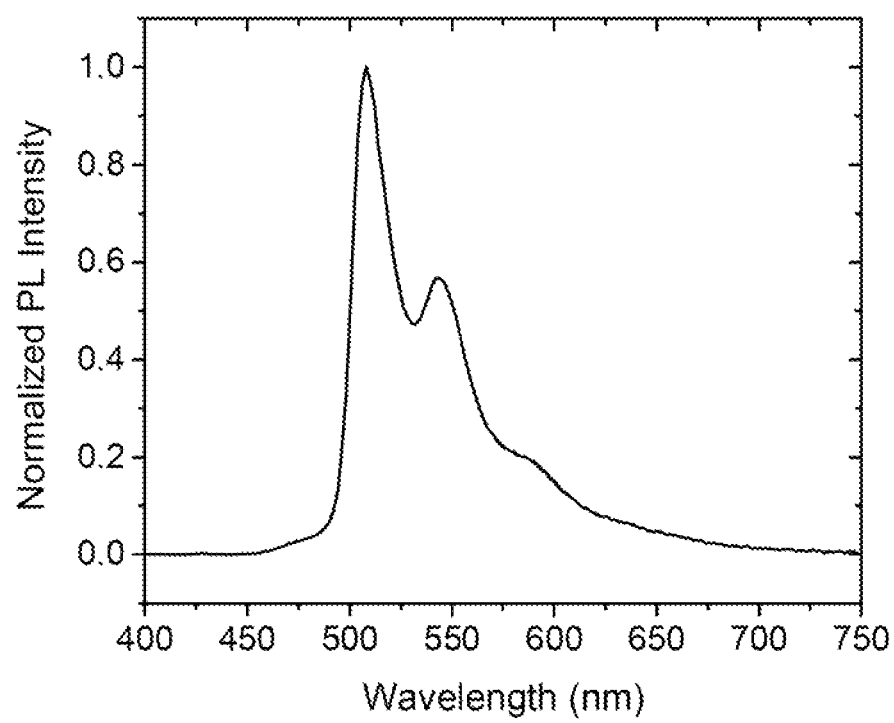
FIG. 4 shows the solution photoluminescence spectrum of Compound 99 in 2-methyl-tetrahydrofuran at room temperature.

FIG. 4 shows the solution photoluminescence spectrum of Compound 99 in 2-methyl-tetrahydrofuran at room temperature. Compound 99 has a Peak maximum of 502 nm which is suitable for being a green dopant in OLED display. Furthermore, the half width of the peak maximum is only 30 nm; which has an excellent color purity for OLED application. The very narrow linewidth might be attributed to a very rigid ligand structure. In other words, the geometry does not change much between the excited state and ground state. The redox property is listed in the following Table 1 to compare with IrPPY; a standard green emitter for OLEDs. Compound 99 has a shallower HOMO and a deeper LUMO than IrPPY. As a result, Compound 99 has a smaller electrochemical band gap than IrPPY and more saturated green color. In general, a smaller electrochemical band gap can be beneficial for OLEDs since it tends to have better stability toward charges.

TABLE 1

| HOMO/LUMO comparison via Cyclic Voltammetry data | | | |
|---|---|---|---|
| Oxidation potential | Reduction Potential | Gap (ev) | T1 |
| 0.2 V (Compound 99) | −2.33 V | 2.53 | 502 nm |
| 0.3 V (IrPPY) | −2.7 V | 3 | 510 nm |

The reduction potentials are based on values measured from differential pulsed volmammetry and are reported relative to a ferrocence/ferrocenium redox couple used as an internal reference (0.45V vs SCE). The following condition was applied for electrochemical measurement: Anhydrous DMF was used as the solvent under inert atmosphere and 0.1M tetra(n-butyl)ammonium hexafluorophosphate was used as the supporting electrolyte; a glassy carbon rod was used as the working electrode; a platinum wire was used as the counter electrode; and a silver wire was used as the reference electrode.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A device comprising one or more organic light emitting devices, at least one of the organic light emitting devices comprising:
an anode;
a cathode; and
an organic layer, disposed between the anode and the cathode, comprising a host and compound having a Pt tetradentate structure, having the formula:

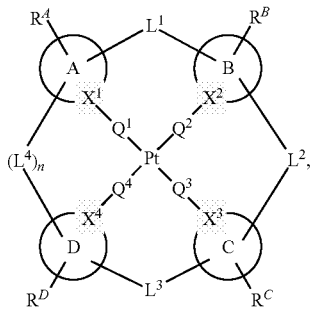

Formula I wherein rings A, B, C, and D each independently represent a 5-membered or 6-membered carbocyclic or heterocyclic ring;
wherein $R^A$, $R^B$, $R^C$, and $R^D$ each independently represent mono, di, tri, or tetra-substitution, or no substitution;
wherein $L^1$, $L^2$, and $L^3$ are each independently selected from the group consisting of a direct bond, BR, NR, PR, O, S, Se, C=O, S=O, $SO_2$, CRR', SiRR', GeRR', and combinations thereof,
wherein when n is 1, $L^4$ is selected from the group consisting of a direct bond, BR, NR, PR, O, S, Se, C=O, S=O, $SO_2$, CRR', SiRR', GeRR', and combinations thereof,
when n is 0, $L^4$ is not present;
wherein $R^A$, $R^B$, $R^C$, $R^D$, R, and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxylic acids, ester, nitrile, isonitrile, sulfanyl, phosphino, and combinations thereof,
wherein any adjacent $R^A$, $R^B$, $R^C$, $R^D$, R, and R' are optionally joined to form a ring;
wherein $X^1$, $X^2$, $X^3$, and $X^4$ each independently selected from the group consisting of carbon and nitrogen;
wherein one of $Q^1$, $Q^2$, $Q^3$, and $Q^4$ is oxygen, the remaining three of $Q^1$, $Q^2$, $Q^3$, and $Q^4$ each represents a direct bond so that Pt directly bonds to three of $X^1$, $X^2$, $X^3$, and $X^4$; and
wherein when $L^1$, $L^2$, $L^3$, or $L^4$ represents a direct bond, the direct bond is not a C—C bond.

2. The device of claim 1, wherein two of $X^1$, $X^2$, $X^3$, and $X^4$ that directly bond to Pt are carbon thus forming Pt—C bonds, and one of $X^1$, $X^2$, $X^3$, and $X^4$ that directly bond to Pt is nitrogen.

3. The device of claim 2, wherein the two Pt—C bonds are in cis configuration.

4. The device of claim 1, wherein $L^1$, $L^2$, and $L^3$ are each independently selected from the group consisting of a direct bond, NR, O, CRR', SiRR', and combinations thereof, and
wherein when n is 1, $L^4$ is selected from the group consisting of a direct bond, NR, O, CRR', SiRR', and combinations thereof.

5. The device of claim 1, wherein R and R' are each independently selected from the group consisting of hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, and combinations thereof.

6. The device of claim 1, wherein the compound has at least one Pt-carbene bond.

7. The device of claim 1, wherein n is 0.

8. The device of claim 1, wherein n is 1.

9. The device of claim 1, wherein one of the rings A, B, C, and D is phenyl when said ring is bonded to one of the $Q^1$, $Q^2$, $Q^3$, and $Q^4$ that is oxygen.

10. The device of claim 1, wherein the rings A, B, C, and D are each independently selected from the group consisting of phenyl, pyridine, and imidazole.

11. The device of claim 1, wherein when $L^1$, $L^2$, $L^3$, or $L^4$ represents a direct bond, the direct bond is a C—N bond.

12. The device of claim 1, wherein at least one of $L^1$, $L^2$, $L^3$, and $L^4$ is not a direct bond.

13. The device of claim 1, wherein the compound is selected from the group consisting of

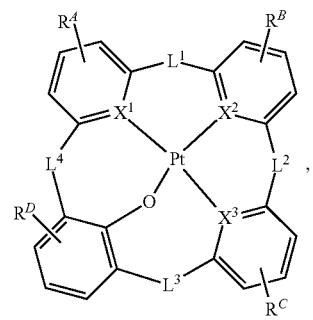

-continued

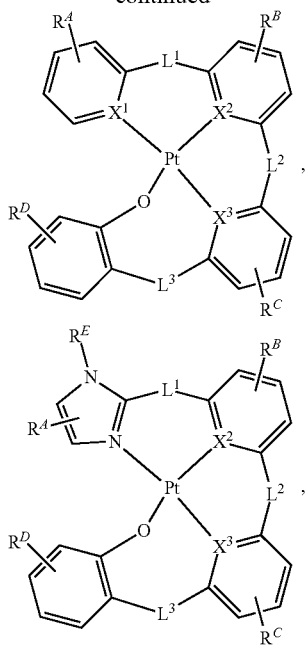

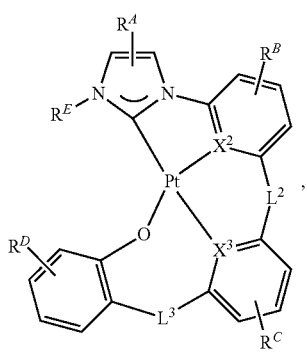

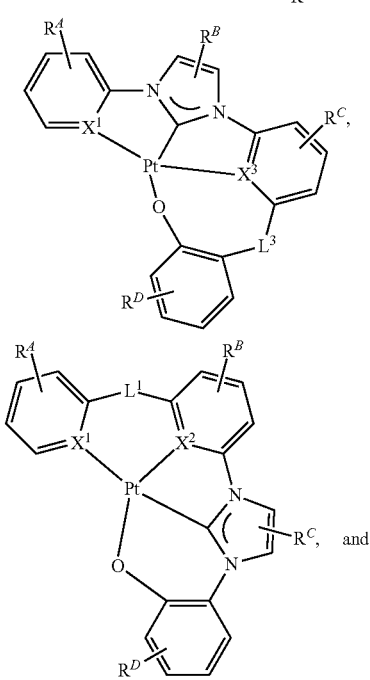

-continued

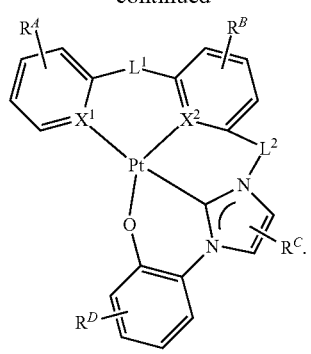

14. The device of claim 1, wherein the host comprises at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, aza-dibenzoselenophene, arylcarbazole, aryltriphenylene, poly-fused heteroaryl, donor-acceptor type, indolocarbazole, 5-membered ring electron deficient heterocycles, tetraphenylene, silicon aryl, germanium aryl.

15. The device of claim 14, wherein the host comprises at least one chemical group selected from the group consisting of triphenylene, carbazole, dibenzothiphene, dibenzofuran, dibenzoselenophene, arylcarbazole, aryltriphenylene, donor-acceptor type, indolocarbazole, tetraphenylene, silicon aryl, and germanium aryl.

16. The device of claim 14, wherein the host comprises at least one chemical group selected from the group consisting of aza-triphenylene, aza-carbazole, aza-dibenzothiophene, aza-dibenzofuran, aza-dibenzoselenophene, poly-fused heteroaryl, and 5-membered ring electron deficient heterocycles.

17. The device of claim 14, wherein the host is selected from the group consisting of

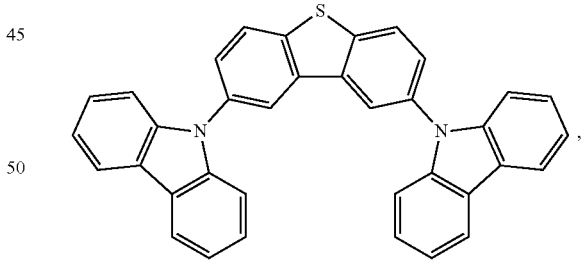

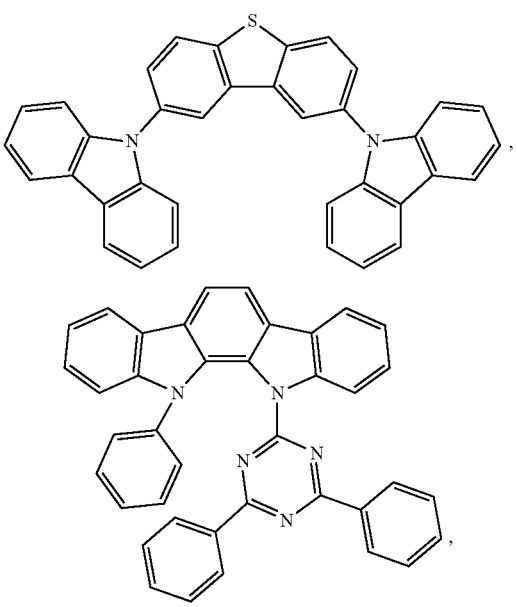

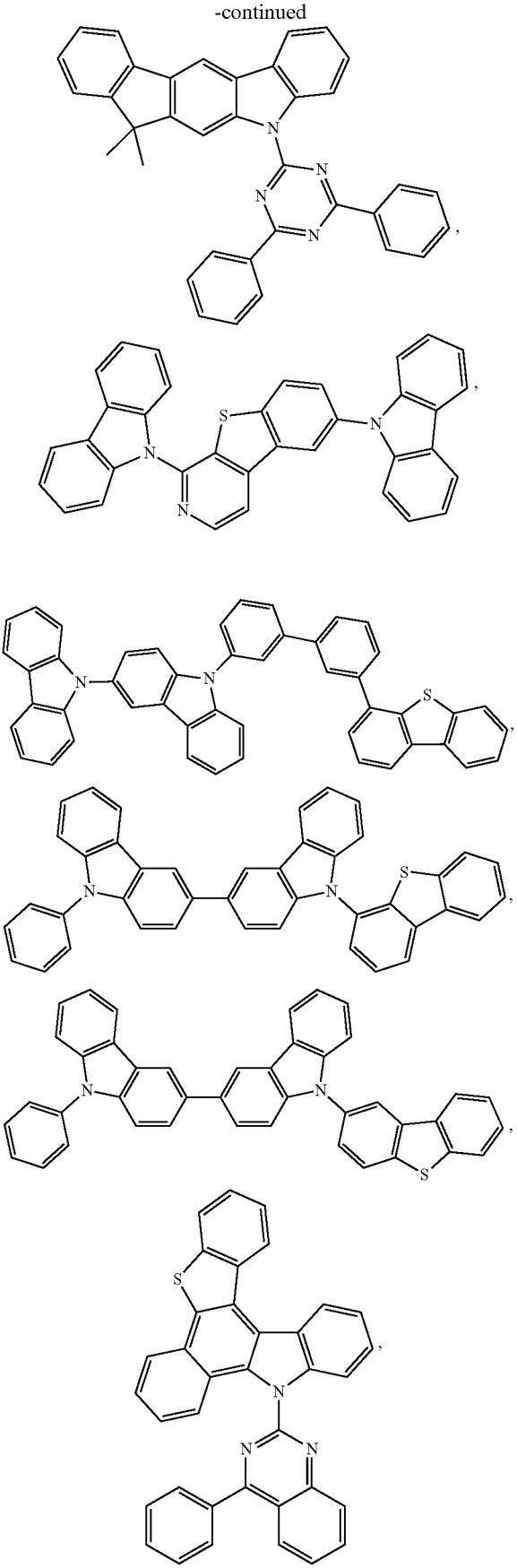
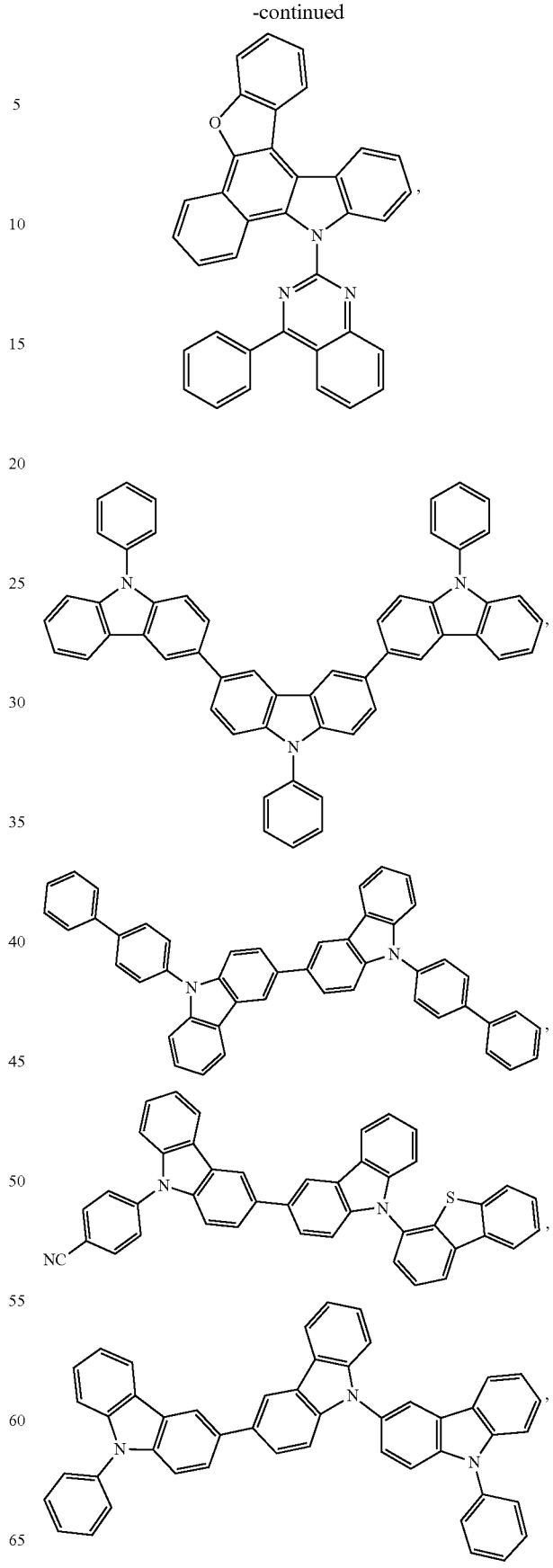

141
-continued

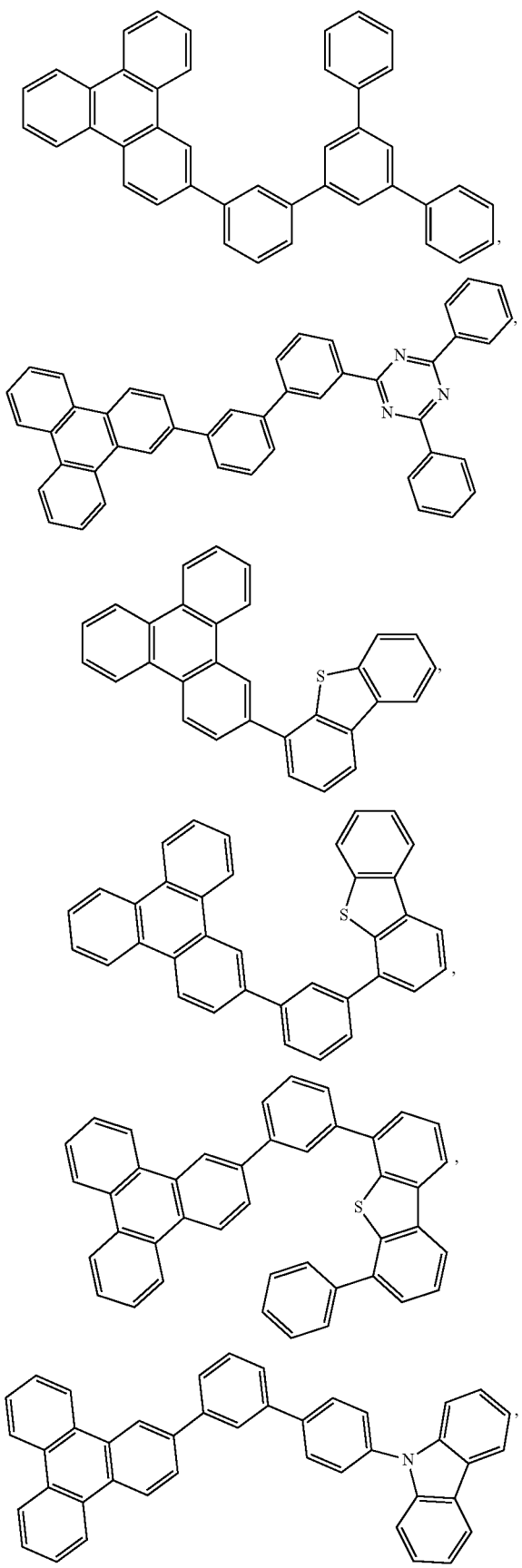

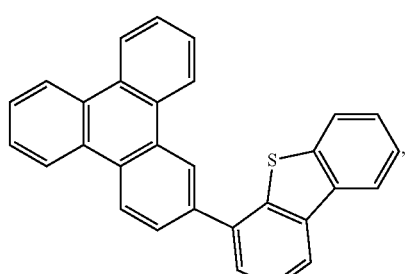

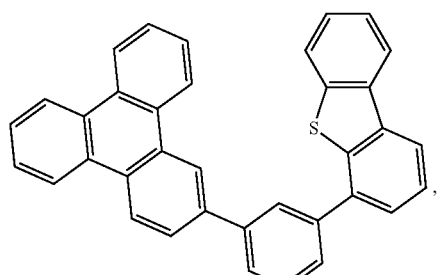

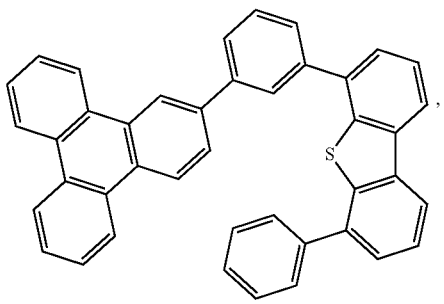

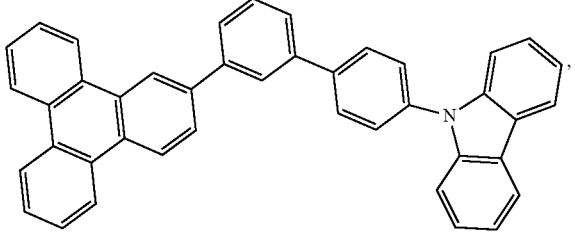

142
-continued

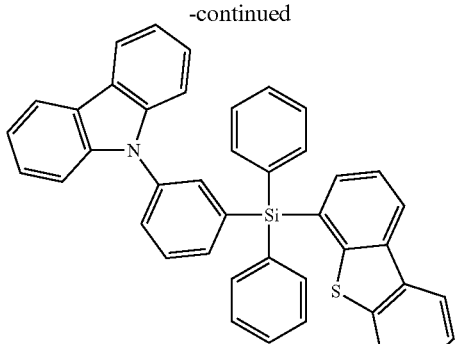

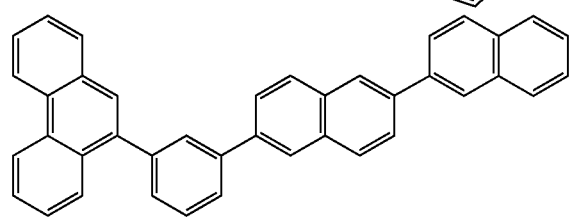

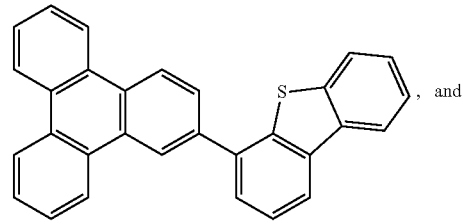

combinations thereof.

18. An emissive layer comprising a compound having a Pt tetradentate structure, having the formula:

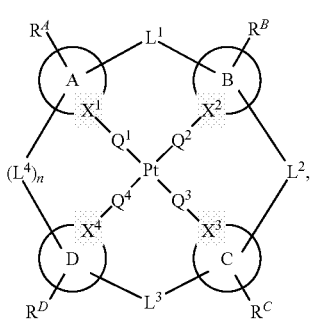

Formula I wherein rings A, B, C, and D each independently represent a 5-membered or 6-membered carbocyclic or heterocyclic ring;
wherein $R^A$, $R^B$, $R^C$, and $R^D$ each independently represent mono, di, tri, or tetra-substitution, or no substitution;
wherein $L^1$, $L^2$, and $L^3$ are each independently selected from the group consisting of a direct bond, BR, NR, PR, O, S, Se, C=O, S=O, $SO_2$, CRR', SiRR', GeRR', and combinations thereof,
wherein when n is 1, $L^4$ is selected from the group consisting of a direct bond, BR, NR, PR, O, S, Se, C=O, S=O, $SO_2$, CRR', SiRR', GeRR', and combinations thereof,
when n is 0, $L^4$ is not present;
wherein $R^A$, $R^B$, $R^C$, $R^D$, R, and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxylic acids, ester, nitrile, isonitrile, sulfanyl, phosphino, and combinations thereof, wherein any adjacent $R^A$, $R^B$, $R^C$, $R^D$, R, and R' are optionally joined to form a ring;

wherein $X^1$, $X^2$, $X^3$, and $X^4$ are each independently selected from the group consisting of carbon and nitrogen;

wherein one of $Q^1$, $Q^2$, $Q^3$, and $Q^4$ is oxygen, the remaining three of $Q^1$, $Q^2$, $Q^3$, and $Q^4$ each represent a direct bond so that Pt directly bonds to three of $X^1$, $X^2$, $X^3$, and $X^4$; and wherein when $L^1$, $L^2$, $L^3$, or $L^4$ represents a direct bond, the direct bond is not a C—C bond.

19. A consumer product comprising one or more organic light emitting devices, at least one of the organic light emitting devices comprising:

an anode;

a cathode; and an organic layer, disposed between the anode and the cathode, comprising a host and a compound having a Pt tetradentate structure, having the formula:

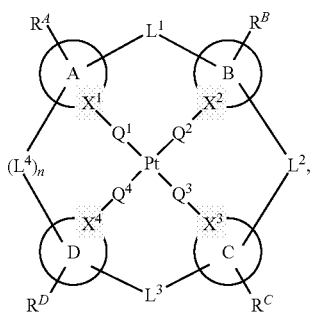

Formula I wherein rings A, B, C, and D each independently represent a 5-membered or 6-membered carbocyclic or heterocyclic ring;

wherein $R^A$, $R^B$, $R^C$, and $R^D$ each independently represent mono, di, tri, or tetra-substitution, or no substitution;

wherein $L^1$, $L^2$, and $L^3$ are each independently selected from the group consisting of a direct bond, BR, NR, PR, O, S, Se, C=O, S=O, SO$_2$, CRR', SiRR', GeRR', and combinations thereof;

wherein when n is 1, $L^4$ is selected from the group consisting of a direct bond, BR, NR, PR, O, S, Se, C=O, S=O, SO$_2$, CRR', SiRR', GeRR', and combinations thereof, when n is 0, $L^4$ is not present;

wherein $R^A$, $R^B$, $R^C$, $R^D$, R, and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxylic acids, ester, nitrile, isonitrile, sulfanyl, phosphino, and combinations thereof, wherein any adjacent $R^A$, $R^B$, $R^C$, $R^D$, R, and R' are optionally joined to form a ring;

wherein $X^1$, $X^2$, $X^3$, and $X^4$ each independently selected from the group consisting of carbon and nitrogen;

wherein one of $Q^1$, $Q^2$, $Q^3$, and $Q^4$ is oxygen, the remaining three of $Q^1$, $Q^2$, $Q^3$, and $Q^4$ each represents a direct bond so that Pt directly bonds to three of $X^1$, $X^2$, $X^3$, and $X^4$; and wherein when $L^1$, $L^2$, $L^3$, or $L^4$ represents a direct bond, the direct bond is not a C—C bond.

20. The consumer product of claim 19, wherein the consumer product is selected from the group consisting of flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, micro-displays, 3-D displays, vehicles, a wall, theater or stadium screen, and a sign.

* * * * *